United States Patent
Ghosh et al.

(10) Patent No.: US 9,265,796 B2
(45) Date of Patent: Feb. 23, 2016

(54) METHODS OF TREATING OR PREVENTING RHEUMATIC DISEASE

(75) Inventors: Peter Ghosh, Fairlight (AU); Silviu Itescu, Melbourne (AU)

(73) Assignee: MESOBLAST, INC., New York, NY (US)

(*) Notice: Subject to any disclaimer, the term of this patent is extended or adjusted under 35 U.S.C. 154(b) by 0 days.

(21) Appl. No.: 14/130,647

(22) PCT Filed: Jul. 4, 2012

(86) PCT No.: PCT/AU2012/000799
§ 371 (c)(1),
(2), (4) Date: May 20, 2014

(87) PCT Pub. No.: WO2013/003899
PCT Pub. Date: Jan. 10, 2013

(65) Prior Publication Data
US 2014/0271567 A1    Sep. 18, 2014

(30) Foreign Application Priority Data

Jul. 4, 2011  (AU) ................................ 2011902655

(51) Int. Cl.
*A01N 63/00*   (2006.01)
*A61K 35/28*   (2015.01)
*C12N 5/0775*  (2010.01)

(52) U.S. Cl.
CPC .............. *A61K 35/28* (2013.01); *C12N 5/0663* (2013.01)

(58) Field of Classification Search
None
See application file for complete search history.

(56) References Cited

FOREIGN PATENT DOCUMENTS

| WO | WO 2006/032092 A1 | 3/2006 |
| WO | WO 2008/036374 A2 | 3/2008 |
| WO | WO 2008/156685 A2 | 12/2008 |
| WO | WO 2009/155656 A1 | 12/2009 |
| WO | WO 2010/025506 A1 | 3/2010 |
| WO | WO 2012/001124 A1 | 1/2012 |

OTHER PUBLICATIONS

Acosta et al., Neurosurg Focus, 2005, vol. 19, No. 3, p. 1-6.*
Miura et al., PNAS, 2005, vol. 102, No. 39, p. 14022-14027.*
Kemp et al., Leukemia & Lymphoma, 2005, vol. 46, No. 11, p. 1531-1544.*
Minaur et al. (2002). Methotrexate in the treatment of rheumatoid arthritis. I. In vitro effects on cells of the osteoblast lineage. *Rheumatology*, 41(7), 735-740.
Jones et al. (2002). Isolation and Characterization of Bone Marrow Multipotential Mesenchymal Progenitor Cells. *Arthritis & Rheumatism*, 46(12), 3349-3360.
Notification of Transmittal of the International Search Report and the Written Opinion of the International Searching Authority, or the Declaration, including an International Search Report and Written Opinion of the International Searching Authority, mailed Aug. 17, 2012 in connection with PCT International Application No. PCT/AU2012/000799, filed Jul. 4, 2012.
Notification Concerning Transmittal of International Preliminary Report on Patentability (Chapter I of the Patent Cooperation Treaty), including an International Preliminary Report on Patentability and Written Opinion of the International Searching Authority, mailed Jan. 16, 2014 by the International Bureau of WIPO in connection with PCT International Application No. PCT/AU2012/000799, filed Jul. 4, 2012.

* cited by examiner

*Primary Examiner* — Kade Ariani
(74) *Attorney, Agent, or Firm* — John P. White; Cooper & Dunham LLP

(57) ABSTRACT

The present disclosure provides a method for treating or preventing a rheumatic disease, comprising administering a population of cells enriched for STRO-1$^+$ cells and/or progeny thereof and/or soluble factors derived therefrom.

16 Claims, 26 Drawing Sheets

CD14 scoring system
(intima scoring scheme after Mo et al, 2011)

| Intima score | % CD14 cells |
|---|---|
| 0 | absent |
| 1 | 1-25% |
| 2 | 26-50% |
| 3 | 51-75% |
| 4 | 76-100% |

Figure 9A

Discrete cell scoring scheme
applied to CD4, CD8, Gamma-delta TCR, CD79a, and Ki-67

| Subset score | Incidence |
| --- | --- |
| 0 | absent |
| + | A few cells in the entire section |
| ++ | Occasional cells or a small cluster |
| +++ | More numerous cells and/or clusters |
| ++++ | Numerous individual cells or clusters/large cluster or clusters |

Figure 9B

Cytokine and adhesion molecule scoring system applied to VCAM-1, IL-6, IL-10, IL-1β, IL-17, TNF-α, and interstitial CD14

| Intima score | Description | Tissue score | Description |
|---|---|---|---|
| 0 | Unstained | 0 | Unstained |
| 1 | A few, or weakly stained cells | 1 | A few scattered cells |
| 2 | Stronger stained | 2 | Occasional cells or a small cluster |
| 3 | Thickened OR densely stained | 3 | More numerous cells and/or clusters |
| 4 | Thickened AND densely stained | 4 | Widespread or densely stained cells |

Figure 9C

CD14 cells

Untreated control left synovium

B1853 score: intima 3, tissue 4

Low dose MPC Group left synovium

B2526 score: intima 2, tissue 1

Mid dose MPC Group left synovium

W4094 score: intima 3, tissue 2

High dose MPC Group left synovium

B2149 score: intima 2, tissue 1

IL-6

Untreated left synovium Control Group

W4561 scores: intima 3, tissue 3

Vascular endothelium    Vascular smooth muscle left synovium High dose MPC Group

B2149 scores: intima 0, tissue 1

Vascular endothelium

IL-17

Untreated left synovium Control Group

W1747 scores: intima 3, tissue 2 left synovium High dose MPC Group

B2149 scores: intima 1, tissue 1

IL-10

Untreated left synovium Control Group

W2833 scores: Intima 0, tissue 0 left synovium High dose MPC Group

B2230 scores: Intima 1, tissue 0

METHODS OF TREATING OR PREVENTING RHEUMATIC DISEASE

CROSS-REFERENCE TO RELATED APPLICATIONS

This application is a §371 national stage of PCT International Application No. PCT/AU2012/000799, filed Jul. 4, 2012, claiming priority of Australian Patent Application No. 2011902655, filed Jul. 4, 2011, the contents of each of which are hereby incorporated by reference in their entirety.

REFERENCE TO SEQUENCE LISTING

This application incorporates-by-reference nucleotide and/or amino acid sequences which are present in the file named "140102_2251_85874_Substitute_Sequence_Listing_BI.txt," which is 7.37 kilobytes in size, and which was created Dec. 30, 2013 in the IBM-PC machine format, having an operating system compatibility with MS-Windows, which is contained in the text file filed Jan. 2, 2014 as part of this application.

FIELD

The present invention relates to methods for treating or preventing rheumatic diseases.

BACKGROUND

Rheumatic diseases are a class of common diseases generally called "arthritis", which are often associated with or caused by an autoimmune response. This class of diseases includes rheumatoid arthritis, spondyloarthropathies (e.g., ankylosing spondylitis), Sjorgren Syndrome (Sicca Syndrome), Reiter's disease, psoriatric arthritis, enteric arthritis (joint problems associated with inflammatory bowel disease), sacroiliitis or spondylitis), and osteoarthritis.

According to the Center for Disease Control (CDC), approximately 50 million adults have been diagnosed with some form of arthritis in USA alone. This number is predicted to increase to 67 million adults by 2030. The CDC estimates that the cost of arthritis in USA was approximately US$80.8 billion for treatments for arthritis and approximately US$47 billion in indirect costs (e.g., lost earnings). The total cost $127.8 billion was 1.2% of the US gross domestic product in 2003.

Rheumatoid Arthritis and Osteoarthritis

Rheumatoid arthritis (RA) is a painful chronic systemic disease characterized by extensive synovial inflammation accompanied by destruction of joint cartilage and bone. The clinical course of RA is variable and often shows a remitting pattern but if progressive inevitably leads to joint deformity and impaired function. Three forms of RA can be distinguished: mild, self-limiting disease; mildly progressive disease; and aggressive disease which is difficult to control with medication, and is characterized by functional decline and radiologic deterioration of the joints, e.g., joint space narrowing and cartilage erosions, particularly beneath the proliferating inflamed synovium referred to as pannus. In accordance with the systemic nature of the disease, there are extra-articular manifestations which include vasculitis, alveolitis, and ocular disease. Prevalence of the disease as reported in the literature is approximately 1% of the U.S. population, with women accounting for two-thirds of all cases.

The onset of RA is often insidious with fatigue, anorexia, generalized weakness, and musculoskeletal pain. Specific symptoms appear later. Several joints, usually in a symmetrical fashion, are affected. Most often these are joints of the hands, wrists, knees, and feet. Joints are painful and swollen, and motion is limited. Morning stiffness of more than one hour is a very typical finding. With persistent inflammation, a variety of deformities develop which include most typically radial deviation of the wrist and hyperextension or flexion of the proximal interphalangeal joints; other deformities occur as well. Atrophy of skeletal muscle sets in. In approximately 20 to 30% of all patients, there is development of rheumatoid nodules on periarticular structures or sites of trauma, but they are usually of limited clinical significance. The nodules may be found in other structures such as the pleura or the meninges. Rheumatoid vasculitis can affect nearly all organ systems (lung, gastro-intestinal-tract, liver, spleen, pancreas, lymph nodes, testis, and the eye).

There is no curative treatment for RA. All drug regimens primarily attempt to relieve the symptoms and the inflammation. Aspirin and other nonsteroidal anti-inflammatory drugs (NSAIDs) with a rapid onset of action are the first line of treatment. Oral and injectable glucocorticoids are added to the drug regimen if necessary. The third line of treatment includes disease modifying antirheumatic drugs (DMARDs); they have a slow onset of action, in some cases several months. DMARDs include azathioprine, sulphasalazine, gold, D-penicillamine, hydroxychloroquine, methotrexate, and cyclosporine. The more recent addition of biological drugs, such as Enbrel®, Remicade® and Humira® has provided an alternative mode of therapy, however regular use of these products can suppress the immuno defence system- and has been associated with increased incidence of opportunistic infections and diseases such as tuberculosis.

Osteoarthritis (OA) is the most common form of arthritis in Western populations. Knee OA, characterized clinically by pain and functional disability, is the leading cause of chronic disability among the elderly in the US.

Pathologically, the most striking changes in OA are focal loss of articular cartilage and marginal and central new bone formation. However, OA is not simply a disease of articular cartilage and the subchondral bone. Rather, it is a disease. of the synovial joint, with alterations also found in the synovium, capsule, ligaments, periarticular muscle, and sensory nerves.

Although OA was once considered a non-inflammatory arthropathy, patients often present with signs and symptoms consistent with local inflammation and synovitis, and recent evidence from preclinical and clinical studies supports the role of inflammation and inflammatory mediators in its pathophysiology.

Current treatment of osteoarthritis includes non-medicinal therapy, medicinal therapy, and surgical treatments. Non-medicinal treatments include exercise, and weightloss, programs, thermal treatment, and assistive devices or bracing. For knee OA, range-of-motion and strengthening exercises are geared toward reduction of impairment, improvement of function; and joint protection. Medications include analgesics (e.g., acetaminophen), non-steroidal anti-inflammatory drugs (NSAIDS) that are either non-selective cyclooxygenase (COX) inhibitors or selective inhibitors of the COX-2 enzyme, injected intra-articular corticosteroids or visco-supplementation, and proven or putative disease-modifying osteoarthritis drugs (DMOADs). Surgical procedures include joint debridement and lavage, and lastly total knee arthroplasty.

The most commonly used medicinal treatments for knee OA typically provide less than 50% relief of pain. For example, use of acetaminophen, selective NSAIDs or non-selective NSAIDs typically results in mean improvements in knee OA pain of no more than 30 points from a baseline of about 70 points using 100 point (100-mm) visual analog scales. Thus, there is substantial room for improvement in the pain management of knee OA. Further, no therapy has been demonstrated to retard the progression of structural degradation.

Ankylosing Spondylitis

Ankylosing spondylitis (AS) is a chronic, progressive, inflammatory disease with considerable impact on patient functioning, well-being, and disability. The prevalence of AS has traditionally been estimated in the range of 0.1-1.9%, with more males affected than females As a chronic disease of the axial skeleton and large peripheral joints, AS causes inflammatory back pain and stiffness and it is associated with other inflammatory diseases of the skin, eyes and intestines. In severe cases, AS may result in complete spinal fusion, causing extreme physical limitation. Thus, there remains a need for a safe and effective treatment for AS.

As the disease progresses, patients with AS experience pain, joint stiffness, and the eventual loss of spinal mobility. These clinical symptoms and subsequent disease progression result in functional limitations and impairment in health-related quality of life (HRQOL).

No cure exists for AS. Generally, treatment includes trying to relieve pain and stiffness using medications such as NSAIDs, corticosteroids, and DMARDs.

It will be apparent to the skilled artisan that inflammatory joint disease is a class of debilitating diseases having a major impact on society. There is also a need for therapeutics for these diseases.

SUMMARY

In work leading up to the present invention, the inventors sought to determine the effect of mesenchymal progenitor cells (MPCs) on rheumatic diseases. The inventors studied a sheep model of rheumatoid arthritis as a model for rheumatic diseases generally, since many of these diseases share common features, e.g., autoimmunity and the presence of immune cells and inflammatory cytokines in the joint. The inventors have determined that MPCs were effective in reducing histopathological indices of arthritis, such as, synovial hyperplasia, stromal tissue activation and inflammatory cell infiltration. Furthermore, the inventors have shown that administration of MPCs reduces levels of pro-inflammatory cytokines, such as, IL-6, TNF$\alpha$, IL-17 in addition to CD14$^+$ cells, e.g., in synovial tissue. The inventors consider that the ability to reduce levels of these cells and cytokines make MPCs (and/or their progeny and/or soluble factors secreted therefrom) suitable for treating rheumatic diseases, such as, rheumatoid arthritis and/or osteoarthritis.

The inventors have also determined that MPCs provide a prolonged therapeutic benefit, with the effects of a single injection of cells lasting for at least about 30 days.

The inventors have additionally found that MPCs or progeny thereof migrated to the site of pathology of the rheumatic disease. Such migration provides benefits since it permits systemic administration of the cells, which is both easier and can be less difficult and/or less invasive, e.g., compared to administering cells into synovial fluid of a subject.

Ovine MPCs isolated by expression of the marker STRO-3 are functionally equivalent to human MPCs which co-express the markers STRO-3 and STRO-1 (as shown herein in Example 2).

The present disclosure therefore provides a method for treating or preventing an rheumatic disease in a subject, the method comprising administering to the subject a population of cells enriched for STRO-1$^+$ cells and/or progeny thereof and/or soluble factors derived therefrom.

In one example, the rheumatic disease is an autoimmune rheumatic disease

In one example, the rheumatic disease is selected from the group consisting of rheumatoid arthritis, Still's disease (syn. juvenile idiopathic arthritis or juvenile rheumatoid arthritis), ankylosing spondylitis, Reiter's disease, psoriatric arthritis, enteric arthritis, sacroiliitis, spondylitis and osteoarthritis.

In one example, the rheumatic disease is osteoarthritis.

In an exemplary form, the rheumatic disease is rheumatoid arthritis.

In one example, the method comprises administering a population of cells enriched for STRO-1$^{bright}$ cells and/or progeny thereof and/or soluble factors derived therefrom.

In one example, the population enriched for STRO-1$^+$ cells and/or progeny thereof and/or soluble factors derived therefrom are administered systemically. For example, the cells are administered intravenously. In this regard, the inventors have shown that STRO-1$^+$ cells and/or progeny thereof migrate to the site of an inflamed joint in a subject. Thus, the disclosure contemplates administration of the STRO-1$^+$ cells and/or progeny thereof at a site remote from an inflamed joint in a subject.

In one example, the STRO-1$^+$ cells and/or progeny thereof and/or soluble factors derived therefrom are administered in an amount sufficient to reduce IL-6, TNF$\alpha$, IL-17 in addition to CD14$^+$ cells in a subject, e.g., within a joint of a subject, such as within synovial tissue.

Exemplary dosages of the cells include between $0.1 \times 10^6$ to $5 \times 10^6$ STRO-1$^+$ cells and/or progeny thereof. For example, the method comprises administering between $0.3 \times 10^6$ to $2 \times 10^6$ STRO-1$^+$ cells and/or progeny thereof per kilogram.

In one example, the cells are administered at a dose of between about $0.3 \times 10^6$ cells/kg to about $4 \times 10^6$ cells/kg, such as between about $0.3 \times 10^6$ cells/kg to about $2 \times 10^6$ cells/kg.

One form of the method involves administering a low dose of STRO-1$^+$ cells and/or progeny thereof. Such a low dose is, for example, between $0.1 \times 10^5$ to about $0.5 \times 10^6$ STRO-1$^+$ cells/kg, such as about $0.3 \times 10^6$ STRO-1$^+$ cells/kg.

In another example, a high dose of cells is administered to the subject. Exemplary dosages include at least about $1.5 \times 10^6$ cells/kg. For example, a high dose comprises between about $1.5 \times 10^6$ to about $4 \times 10^6$ cells/kg. For example, a high dose comprises about $1.5 \times 10^6$ or about $2 \times 10^6$ cells/kg. The inventors have shown that such doses provide benefits, e.g., by reducing levels of IL-6, TNF$\alpha$, IL-17 in addition to CD14$^+$ cells.

In one example, the cells are administered at a dose of about 100 million to 300 million cells irrespective of the weight of the patient.

In one example, the cells are administered at a dose of about 100 million to 200 million cells irrespective of the weight of the patient.

In one example, the cells are administered at a dose of about 100 million cells irrespective of the weight of the patient.

In one example, the cells are administered at a dose of about 150 million cells irrespective of the weight of the patient.

In one example, the cells are administered at a dose of about 200 million cells irrespective of the weight of the patient.

In one example, the cells are administered at a dose of about 300 million cells irrespective of the weight of the patient.

In one example, the population enriched for STRO-1+ cells and/or progeny thereof and/or soluble factors derived therefrom are administered once weekly or less often, such as, once every four weeks or less often.

The present disclosure also contemplates numerous administrations of the cells and/or Soluble factors. For example, such a method can involve administering the cells and monitoring the subject to determine when one or more symptoms of an inflammatory joint disease occurs or recurs and administering a further dose of the cells and/or soluble factors. Suitable methods for assessing symptoms of an rheumatic disease will be apparent to the skilled artisan and/or described herein.

In another example, cells and/or soluble factors are administered on a fixed schedule, e.g., once each week or fortnight or three weeks or four weeks or five weeks or six weeks or longer.

In one example, the population enriched for STRO-1+ cells and/or progeny cells are autogeneic or allogeneic and/or the soluble factors can be derived from autogeneic or allogeneic cells.

In one example, the population enriched for STRO-1+ cells and/or progeny cells have been culture expanded prior to administration and/or prior to obtaining the soluble factors.

In one example, the population enriched for STRO-1+ cells are STRO-1$^{bright}$, and/or express tissue non-specific alkaline phosphatase (TNAP) and/or the progeny cells and/or soluble factors are derived from STRO-1+ cells that are STRO-1$^{bright}$ and/or express TNAP.

In one example, the STRO-1+ cells and/or progeny cells thereof and/or soluble factors derived therefrom are administered in the form of a composition comprising said STRO-1+ cells and/or progeny cells thereof and/or soluble factors derived therefrom and a carrier and/or excipient.

In one example, the STRO-1+ cells and/or progeny cells thereof and/or soluble factors derived therefrom are administered together with another compound for treating or preventing an rheumatic disease. In one example, the other compound is a disease-modifying anti-rheumatic drug (DMARD). In one example, the DMARD is selected from the group consisting of hydroxycloroquine, sulfasalazine, methotrexate, leflunomide, azathioprine, D-penicillamine, gold salts minocycline, cyclosporine and TNF-inhibitors.

In one example, the DMARD is selected from the group consisting of azathioprine, chloroquine, hydroxychloroquine, leflunomide, methotrexate and sulfasalazine. In one example, the DMARD is methotrexate.

In another example, the DMARD is an anti-TNF antibody (e.g., infliximab, golimumab or adalimumab) or a soluble TNF receptor (e.g., etanercept).

In one example, the STRO-1+ cells and/or progeny cells thereof and/or soluble factors derived therefrom are administered together with a B cell depleting agent. In one example, the B cell depleting agent is an anti-CD20 antibody, such as rituximab or ofatumumab.

In one example, the STRO-1+ cells and/or progeny cells thereof and/or soluble factors derived therefrom are administered to a subject suffering from rheumatoid arthritis and receiving treatment with methotrexate.

In one example, the STRO-1+ cells and/or progeny cells thereof and/or soluble factors derived therefrom are administered as adjunctive and/or concomitant therapy to methotrexate therapy.

In one example, the subject suffers from moderately active rheumatoid arthritis or severely active rheumatoid arthritis or moderately to severely active rheumatoid arthritis.

In one example, the STRO-1+ cells and/or progeny cells thereof are administered to a subject suffering from rheumatoid arthritis and receiving treatment with methotrexate, wherein the cells are administered at a dose of about $1\times10^6$—about $3\times10^6$ cells/kg.

In one example, the STRO-1+ cells and/or progeny cells thereof are administered to a subject suffering from rheumatoid arthritis and receiving treatment with methotrexate, wherein the cells are administered at a dose of about $1.5\times10^6$—about $2\times10^6$ cells/kg.

In one example, the STRO-1+ cells and/or progeny cells thereof are administered to a subject suffering from rheumatoid arthritis and receiving treatment with methotrexate, wherein the cells are administered at a dose of about $1.5\times10^6$ cells/kg.

In one example, the STRO-1+ cells and/or progeny cells thereof are administered to a subject suffering from rheumatoid arthritis and receiving treatment with methotrexate, wherein the cells are administered at a dose of about $2\times10^6$ cells/kg.

In one example, the STRO-1+ cells and/or progeny cells thereof are administered to a subject suffering from rheumatoid arthritis and receiving treatment with methotrexate, wherein the cells are administered at a dose of between about 100 million cells to about 300 million cells irrespective of the weight of the patient, such as, between about 100 million cells to about 200 million cells irrespective of the weight of the patient.

In one example, the STRO-1+ cells and/or progeny cells thereof are administered systemically, e.g., intravenously.

Thus, in one example, the present disclosure provides a method for treating or preventing osteoarthritis in a subject, the method comprising intravenously (or systemically) administering to the subject a population of cells enriched for STRO-1+ cells and/or progeny thereof and/or soluble factors derived therefrom. Exemplary cells, dosages and combination treatments are described herein and are to be taken to apply mutatis mutandis to the present example of the disclosure.

In another example, the present disclosure provides a method for treating or preventing rheumatoid arthritis in a subject, the method comprising intravenously (or systemically) administering to the subject a population of cells enriched for STRO-1+ cells and/or progeny thereof and/or soluble factors derived therefrom. Exemplary cells, dosages and combination treatments are described herein and are to be taken to apply mutatis mutandis to the present example of the disclosure.

The present disclosure additionally provides a population of cells enriched for STRO-1+ cells and/or progeny thereof and/or soluble factors derived therefrom for use in the treatment or prevention of a rheumatic disease in a subject.

The present disclosure additionally provides for use of a population of cells enriched for STRO-1+ cells and/or progeny thereof and/or soluble factors derived therefrom in the manufacture of a medicament for treating- or preventing a rheumatic disease in a subject.

KEY TO SEQUENCE LISTING

SEQ ID NO: 1 oligonucleotide for amplifying nucleic acid encoding GAPDH
SEQ ID NO: 2 oligonucleotide for amplifying nucleic acid encoding GAPDH
SEQ ID NO: 3 oligonucleotide for amplifying nucleic acid encoding SDF-1

SEQ ID NO: 4 oligonucleotide for amplifying nucleic acid encoding SDF-1
SEQ ID NO: 5 oligonucleotide for amplifying nucleic acid encoding IL-1β
SEQ ID NO: 6 oligonucleotide for amplifying nucleic acid encoding IL-1β
SEQ ID NO: 7 oligonucleotide for amplifying nucleic acid encoding FLT-1
SEQ ID NO: 8 oligonucleotide for amplifying nucleic acid encoding FLT-1
SEQ ID NO: 9 oligonucleotide for amplifying nucleic acid encoding TNF-α
SEQ ID NO: 10 oligonucleotide for amplifying nucleic acid encoding TNF-α
SEQ ID NO: 11 oligonucleotide for amplifying nucleic acid encoding KDR
SEQ ID NO: 12 oligonucleotide for amplifying nucleic acid encoding KDR
SEQ ID NO: 13 oligonucleotide for amplifying nucleic acid encoding RANKL
SEQ ID NO: 14 oligonucleotide for amplifying nucleic acid encoding RANKL
SEQ ID NO: 15 oligonucleotide for amplifying nucleic acid encoding Leptin
SEQ ID NO: 16 oligonucleotide for amplifying nucleic acid encoding Leptin
SEQ ID NO: 17 oligonucleotide for amplifying nucleic acid encoding CBFA-1
SEQ ID NO: 18 oligonucleotide for amplifying nucleic acid encoding CBFA-1
SEQ ID NO: 19 oligonucleotide for amplifying nucleic acid encoding PPARγ2
SEQ ID NO: 20 oligonucleotide for amplifying nucleic acid encoding PPARγ2
SEQ ID NO: 21 oligonucleotide for amplifying nucleic acid encoding OCN
SEQ ID NO: 22 oligonucleotide for amplifying nucleic acid encoding OCN
SEQ ID NO: 23 oligonucleotide for amplifying nucleic acid encoding MyoD
SEQ ID NO: 24 oligonucleotide for amplifying nucleic acid encoding MyoD
SEQ ID NO: 25 oligonucleotide for amplifying nucleic acid encoding SMMHC
SEQ ID NO: 26 oligonucleotide for amplifying nucleic acid encoding SMMHC
SEQ ID NO: 27 oligonucleotide for amplifying nucleic acid encoding GFAP
SEQ ID NO: 28 oligonucleotide for amplifying nucleic acid encoding GFAP
SEQ ID NO: 29 oligonucleotide for amplifying nucleic acid encoding Nestin
SEQ ID NO: 30 oligonucleotide for amplifying nucleic acid encoding Nestin
SEQ ID NO: 31 oligonucleotide for amplifying nucleic acid encoding SOX9
SEQ ID NO: 32 oligonucleotide for amplifying nucleic acid encoding SOX9
SEQ ID NO: 33 oligonucleotide for amplifying nucleic acid encoding Collagen type X
SEQ ID NO: 34 oligonucleotide for amplifying nucleic acid encoding Collagen type X
SEQ ID NO: 35 oligonucleotide for amplifying nucleic acid encoding Aggrecan
SEQ ID NO: 36 oligonucleotide for amplifying nucleic acid encoding Aggrecan

BRIEF DESCRIPTION OF THE DRAWINGS

FIG. 9A shows CD 14 scoring system (intima scoring scheme as described in Mo et al., *J Rheumatol.* 38: 2301-2308, 2011).

FIG. 9B shows discrete cell scoring scheme applied to CD4, CD8, Gamma-delta TCR, CD79a and Ki-67.

FIG. 9C shows cytokine and adhesion molecule scoring system applied to VCAM-1, IL-6, IL-10, IL-1β, IL-17, TNFα and interstitial CD14.

DETAILED DESCRIPTION

General Techniques and Selected Definitions

Figure 1:
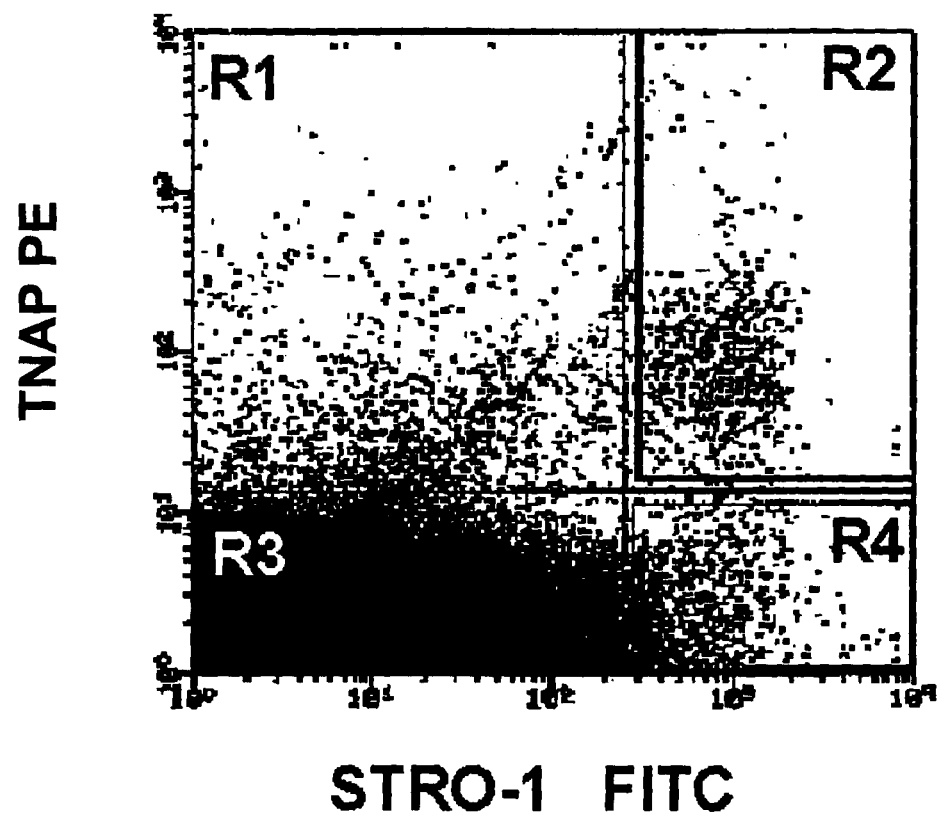
FIG. 1. Co-expression of TNAP(STRO-3) and the Mesenchymal Precursor Cell Marker, STRO-1$^{bright}$ by Adult Human bone marrow morphonuclear cells (BMMNC). Dual-color immunofluorescence and flow cytometry was performed by incubation of STRO-1 MACS-selected BMMNC and indirectly labeled with a goat anti-murine IgM antibody coupled to FITC (x axis), and STRO-3 mAb (murine IgG1) indirectly labeled with a goat anti-murine IgG coupled to PE (y axis). The dot plot histogram represents 5×10$^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1$^+$ cells failed to react with the STRO-3 mAb.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment or example described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al., pp 35-81; Sproat et al, pp 83-115; and Wu et al., pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source. In the context of soluble factors derived from STRO-1$^+$ cells and/or progeny cells thereof, this term shall be taken to mean one or more factors, e.g., proteins, peptides, carbohydrates, etc, produced during in vitro culturing of STRO-1$^+$ cells and/or progeny cells thereof.

As used herein, the term "rheumatic diseases" shall be taken to mean any disease characterized by an inflammatory response in at least one joint in a subject. In one example, the rheumatic disease is caused by or associated with an autoimmune condition. Exemplary rheumatic diseases are known in the art and/or described herein.

As used herein, the term "effective amount" shall be taken to mean a sufficient quantity of STRO-1$^+$ cells and/or progeny cells thereof and/or soluble factors derived therefrom to reduce inflammation and/or the number of inflammatory cells and/or inflammatory cytokines in the joint of a subject that causes or is associated with a rheumatic disease.

As used herein, the term "therapeutically effective amount" shall be taken to mean a sufficient quantity of STRO-1$^+$ cells and/or progeny cells thereof and/or soluble factors derived therefrom to reduce or inhibit one or more symptoms of a rheumatic disease.

As used herein, the term "prophylactically effective amount" shall be taken to mean a sufficient quantity of STRO-1$^+$ cells and/or progeny cells thereof and/or soluble factors derived therefrom to prevent or inhibit or delay the onset of one or more detectable symptoms of an inflammatory joint disease.

As used herein, the term "low dose" shall be understood to mean an amount of STRO-1$^+$ cells and/or progeny thereof less than $1 \times 10^6$ cells/kg, yet still sufficient to reduce inflammation and/or an inflammatory cytokine and/or the number of inflammatory cells in the joint of a subject. For example, a low dose comprises $0.5 \times 10^6$ or fewer cells, or $0.4 \times 10^6$ or fewer cells or $0.3 \times 10^6$ or fewer cells or $0.1 \times 10^6$ or fewer cells per kg.

As used herein, the term "high dose" shall be understood to mean an amount of STRO-1$^+$ cells and/or progeny thereof sufficient to reduce IL-6, TNFα, IL-17 in addition to CD14$^+$ cells in a subject, e.g., within a joint of a subject, such as within synovial tissue, such as more than $1.5 \times 10^6$ cells/kg. For example, a dose comprises between about $1.5 \times 10^6$ to about $4 \times 10^6$ cells/kg. For example, a high dose comprises about $1.5 \times 10^6$ or about $2 \times 10^6$/kg.

As used herein, the term "treat" or "treatment" or "treating" shall be understood to mean administering a therapeutically effective amount of soluble factors and/or cells and reducing or inhibiting at least one symptom of an inflammatory joint, disease.

As used herein, the term "prevent" or "preventing" or "prevention" shall be taken to mean administering a prophylactically effective amount of soluble factors and/or cells and stopping or hindering or delaying the development or progression of an inflammatory joint disease.

As used herein, the term "soluble factors" shall be taken to mean any molecule, e.g., protein; peptide, glycoprotein, glycopeptide, lipoprotein, lipopeptide, carbohydrate, etc. produced by STRO-1$^+$ cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one example of the present invention soluble factors are or are contained within supernatant. Accordingly, any example herein directed to administration of one or more soluble factors shall be taken to apply mutatis mutandis to the administration of supernatant.

As used herein, the term "supernatant" refers to the non-cellular material produced following the in vitro culturing of mesenchymal precursor cells, and/or progeny cells thereof, in a suitable medium, such as, liquid medium. Typically, the supernatant is produced by culturing the cells in the medium under suitable conditions and time, followed by removing the cellular material by a process such as centrifugation. The supernatant may or may not have been subjected to further purification steps before administration. In one example, the supernatant comprises less than $10^5$, such as less than $10^4$, for example, less than $10^3$ and e.g., no live cells.

As used herein, the term "normal or healthy subject" shall be taken to mean a subject that does not suffer from an inflammatory joint disease as assessed by any method known in the art and/or described herein.

As used herein, the term "subject" shall be taken to mean any animal including humans, for example a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). In one example, the mammal is a human or primate. In one example, the mammal is a human. In one example, a subject is eligible for treatment who is experiencing or has experienced one or more signs, symptoms, or, other indicators of inflammatory joint damage, has been diagnosed with inflammatory joint damage, whether, for example, newly diagnosed or previously diagnosed and now experiencing a recurrence or relapse, or is at risk for developing inflammatory joint damage.

Rheumatic Diseases

In one example of the present disclosure, rheumatic diseases are inflammatory joint diseases. Inflammatory joint diseases is used herein in the broadest sense and refers to damage or partial or complete destruction to any part of one or more joints, including the connective tissue and cartilage, where damage includes structural and/or functional damage of any cause and is characterized by inflammation in the joint, and may or may not cause joint pain/arthalgia. This damage may be caused by any condition, such as an autoimmune disease such as arthritis (e.g., acute and chronic arthritis), rheumatoid arthritis including juvenile-onset rheumatoid arthritis, juvenile idiopathic arthritis (JIA), or juvenile RA (JRA), and stages such as rheumatoid synovitis, gout or gouty arthritis, acute immunological arthritis, chronic inflammatory arthritis, degenerative arthritis, type II collagen-induced arthritis, infectious arthritis, septic arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), rheumatic autoimmune disease other than RA, significant systemic involvement secondary to RA (including but not limited to vasculitis, pulmonary fibrosis or Felty's syndrome), seronegative spondyloarthropathy, Lyme disease, mixed connective tissue disease, autoimmune disorders associated with collagen disease.

In one example, the skilled person will understand that an inflammatory joint disease is not an injury to cartilage or bone or joint caused solely by, for example, overuse or a sporting injury or impact to a joint, since these conditions are not diseases.

In one example, the inflammatory joint disease is associated with or caused by an autoimmune disease. An "autoimmune disease" is a disease arising from and directed against a subject's own tissues or organs or a co-segregate or manifestation thereof or resulting condition therefrom. In one example, the inflammatory joint disease is an autoimmune inflammatory joint disease, such as caused by a subject's having an immune response against an antigen that occurs in the subject's joint.

In one example, the inflammatory joint damage is caused by arthritis, such as, rheumatoid arthritis, osteoarthritis, ankylosing spondylitis, or psoriatic arthritis.

In one example, the inflammatory joint disease is rheumatoid arthritis.

In one example, the inflammatory joint disease is osteoarthritis arthritis.

For purposes herein, joints are points of contact between elements of a skeleton (of a vertebrate such as an animal) with the parts that surround and support it and include, but are not limited to, for example, hips, joints between, the vertebrae of the spine, joints between the spine and pelvis (sacroiliac joints), joints where the tendons and ligaments attach to bones, joints between the ribs and spine, shoulders, knees, feet, elbows, hands, fingers, ankles and toes, but especially joints in the hands and feet.

Methods for detecting and/or diagnosing inflammatory joint disease and/or monitoring efficacy of treatment and/or if additional treatment is required or recommended will be apparent to the skilled artisan. For example, comparing the number of tender and swollen joints between baseline and various time points during treatment is a typical way to assess joint status and response to treatment. In the American College of Rheumatology (ACR) joint count for RA (Felson et al. *Arthritis & Rheumatology* 38: 727-735, 1995), 68 joints are assessed for tenderness and 66 for swelling (the hip is not assessed for swelling). In the Disease Activity Score (DAS) employed primarily in Europe, either a 44- or 28-joint count is used in RA. In addition to the joint count, the ACR evaluation criteria include the following elements to comprise a composite score: patient global (on a visual analog scale [VAS]), patient pain, physician global, Health Assessment Questionnaire (HAQ; a measure of function), and an acute-phase reactant (either C-reactive protein or sedimentation rate). An ACR 20 response would constitute a 20% improvement in tender and swollen joint count and a 20% improvement of at least 3 of the other 5 elements in the composite criteria. ACR 50 and 70 responses represent at least a 50% and 70% improvement of these elements. The ACR system only represents change, whereas the DAS system represents both current state of disease activity and change. The DAS scoring system uses a weighted mathematical formula, derived from clinical trials in RA. For example, the DAS 28 is 0.56(T28)+ 0.28(SW28)+0.70(Ln ESR)+0.014 GH wherein T represents tender joint number, SW is swollen joint number, ESR is erythrocyte sedimentation rate, and GH is global health. Various values of the DAS represent high or low disease activity as well as remission, and the change and endpoint score result in a categorization of the patient by degree of response (none, moderate, good).

As used herein, "rheumatoid arthritis" refers to a recognized disease state which may be diagnosed according to the 2000 revised American Rheumatoid Association criteria for the classification of rheumatoid arthritis, or any similar criteria. Physiological indicators of RA include, symmetric joint swelling which is characteristic though not invariable in rheumatoid arthritis. Fusiform swelling of the proximal interphalangeal (PIP) joints of the hands as well as metacarpophalangeal (MCP), wrists, elbows, knees, ankles and metatarsophalangeal (MTP) joints are commonly affected and swelling is easily detected. Pain on passive motion is the most sensitive test for joint inflammation, and inflammation and structural deformity often limits the range of motion for the affected joint. Typical visible changes include ulnar deviation of the fingers at the MCP joints, hyperextension or hyperflexion of the MCP and PIP joints, flexion contractures of the elbows, and subluxation of the carpal bones and toes. The subject with rheumatoid arthritis may or may not be resistant to DMARDs, in that the DMARDs are not effective or fully effective in treating symptoms. Furthermore, the subject may have experienced an inadequate response to previous or current treatment with TNF inhibitors such as etanercept, infliximab and/or adalimumab because of toxicity or inadequate efficacy (for example, etanercept for 3 months at 25 mg twice a week or at least 4 infusions of infliximab at 3 mg/kg) and/or anti-CD20 therapy (e.g., rituximab.

Rheumatoid arthritis can also be diagnosed by the presence of autoantibodies, e.g., rheumatoid factor (antibodies that bind IgG) and/or anti-cyclic citrullinated peptide and/or heterogeneous nuclear ribonucleoprotein A2 (RA33) and/or type II collagen and/or stress proteins (e.g., BiP or hsp90) and/or glucose 6-phophate isomerise (GPI).

"Psoriatic arthritis" or "PsA" is a chronic disease characterized by inflammation of the skin (psoriasis) and joints (arthritis). Psoriasis features patchy, raised, red areas of skin inflammation with scaling and often affects the tips of the elbows and knees, the scalp, the navel, and around the genital areas or anus. Approximately 10% of patients who have psoriasis also develop an associated inflammation of their joints. Patients who have both inflammatory arthritis and psoriasis are diagnosed as having psoriatic arthritis. Psoriatic arthritis is a systemic rheumatic disease that can also cause inflammation in body tissues away from the joints and the skin, such as in the eyes, heart, lungs, and kidneys.

"Ankylosing spondylitis" or "AS" is a form of chronic inflammation of the spine and the sacroiliac joints, which are located in the low back where the sacrum (the bone directly above the tailbone) meets the iliac bones (bones on either side of the upper buttocks). Chronic inflammation in these areas causes pain and stiffness in and around the spine. Over time, chronic spinal inflammation (spondylitis) can lead to a complete cementing together (fusion) of the vertebrae, a process referred to as ankylosis. Ankylosis leads to loss of mobility of the spine. Ankylosing spondylitis is also a systemic rheumatic disease, meaning it can affect other tissues throughout the body. Accordingly, it can cause inflammation in or injury to other joints away from the spine, as well as other organs, such as the eyes, heart, lungs, and kidneys.

MPCs or Progeny Cells, and Supernatant or One or More Soluble Factors Derived Therefrom MPCs are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm.

In one example, the MPCs are multipotential cells which are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironinental conditions established by host tissues. MPCs are multipotential cells are thus non-hematopoietic progenitor cells which divide to yield daughter cells that are either stem cells or are precursor cells which in time will irreversibly differentiate to yield a phenotypic cell.

MPCs are positive for the marker STRO-1 (i.e. MPCs are STRO-1$^+$ cells)

In one example, the STRO-1$^+$ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1$^+$ cells comprises at least about 0.1% or 0.5% or 1% or 2% or 5% or 10% or 15% or 20% or 25% or 30% or 50% or 75% STRO-1$^+$ cells. In this regard, the term "population of cells enriched for STRO-1$^+$ cells" will be taken to provide explicit support for the term "population of cells comprising X % STRO1$^+$ cells", wherein X % is a percentage as recited herein. The STRO-1$^+$ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-1$^+$ cells in a selectable form. In this regard, the term "selectable form" will be understood to mean that the cells express a marker (e.g., a cell surface marker) permitting selection of the STRO-1$^+$ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1$^+$ does not necessarily mean that the cells are selected by STRO-1 expression. In one example, the cells are selected based on at least STRO-3 expression, e.g., they are STRO-3$^+$ (TNAP$^+$).

Reference to selection of a cell or population thereof does not require selection from a specific tissue source. As described herein STRO-1$^+$ cells can be selected from or isolated from or enriched from a large variety of sources. That said, in some examples, these terms provide support for selection from any tissue comprising STRO-1$^+$ cells (e.g., MPCs) or vascularized tissue or tissue comprising pericytes (e.g., STRO-1$^+$ pericytes) or any one or more of the tissues recited herein.

In one example, the cells used in the present invention express one or more markers individually or collectively selected from the group consisting of TNAP$^+$, VCAM-1$^+$, THY-1$^+$, STRO-2$^+$, CD45$^+$, CD146$^+$, 3G5$^+$ or any combination thereof.

By "individually" is meant that the invention encompasses the recited markers or groups of markers separately, and that, notwithstanding that individual markers or groups of markers may not be separately listed herein the accompanying claims may define such marker or groups of markers separately and divisibly from each other.

By "collectively" is meant that the invention encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

For example, the STRO-1$^+$ cells are STRO-1$^{bright}$ (syn. STRO-1$^{bri}$). In one example, the Stro-1$^{bri}$ cells are preferentially enriched relative to STRO-1$^{dim}$ or STRO-1$^{intermediate}$ cells.

For example, the STRO-1$^{bright}$ cells are additionally one or more of TNAP$^+$, VCAM-1$^+$, THY-1$^+$, STRO-2$^+$ and/or CD146$^+$. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630. For example, the mesenchymal precursor cells express a marker of a perivascular cell, e.g., the cells are STRO-1$^+$ or STRO-1$^{bright}$ and/or 3G5$^+$. In one example, the cells are or were previously or are progeny of cells that were isolated from vascularized tissue or organs or parts thereof.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, e.g., levels detected suing an isotype control antibody.

The term "bright", when used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). For example, "bright" cells constitute at least about 0.1% of the most brightly labeled bone marrow mononuclear cells contained in the starting sample. In other examples, "bright" cells constitute at least, about 0.1%, at least about 0.5%, at least about 1%, at least about 1.5%, or at least about 2%, of the most brightly labeled bone marrow mononuclear cells contained in the starting sample. In one example, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1$^+$ cells are capable of giving rise to clonogenic CFU-F.

In one example, a significant proportion of the STRO-1$^+$ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1$^+$ cells are not capable of giving rise, upon culturing, to hematopoietic cells.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used. In another useful example of the invention, cells of a non-human animal (or if the patient is not a human, from another species) are used.

The present invention also contemplates use of supernatant or soluble factors obtained or derived from STRO-1$^+$ cells and/or progeny cells thereof (the latter also being referred, to as expanded cells) which are produced from in vitro culture. Expanded cells of the invention may a have a wide variety of phenotypes depending on the culture conditions (including the number and/or type of stimulatory factors in the culture medium), the number of passages and the like. In certain examples, the progeny cells are obtained after about 2, about 3, about 4, about 5, about 6, about 7; about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an example, progeny cells useful for the methods of the invention are obtained by isolating TNAP$^+$ STRO-1$^+$ cells from bone marrow using magnetic beads labeled with the STRO-3 antibody, and then culture expanding the isolated cells (see Gronthos et al. Blood 85: 929-940, 1995 for an example of suitable culturing conditions).

In one example, such expanded cells (progeny) (for example, at least after 5 passages) can be TNAP$^-$, CC9$^+$, HLA class I$^+$, HLA class II$^-$, CD14$^-$, CD19$^-$, CD3$^-$, CD11a$^-$c$^-$, CD31$^-$, CD86$^-$, CD34$^-$ and/or CD80$^-$. However, it is possible that under different culturing conditions to those described herein that the expression of different markers may vary. Also, whilst cells of these phenotypes may predominate in the expanded cell population it does not mean that there is a minor proportion of the cells do not have this phenotype(s) (for example, a small percentage of the expanded cells may be CC9$^-$). In one example, expanded cells still have the capacity to differentiate into different cell types.

In one example, an expended cell population used to obtain supernatant or soluble factors, or cells per se, comprises cells wherein at least 25%, for example at least 50%, of the cells are CC9$^+$.

In another example, an expanded cell population used to obtain supernatant or soluble factors, or cells per se, comprises cells wherein at least 40%, for example at least 45%, of the cells are STRO-1$^+$.

In a further example, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD 10, CD 13, SCF, PDGF-R, EGF-R, IGF1-R, NGF-R, FGF-R, Leptin-R (STRO-2=Leptin-R), RANKL, STRO-1$^{bright}$ and CD146 or any combination of these markers.

In one example, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{bri}$ and ALP. In one example of the present invention, at least 15%, 20%, 30%, 40%, 50%, 60%, 70%, 80%, 90% or 95% of the administered cells have the phenotype STRO-1$^{bri}$, ALP$^-$. In a further example the MEMPS are positive for one or more of the markers Ki67, CD44 and/or CD49c/CD29, VLA-3, α3β1. In yet a further example the MEMPs do not exhibit TERT activity and/or are negative for the marker CD 18.

The STRO-1+ cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, exemplary methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, with exemplary methods being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. Exemplary separation techniques maximize the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

Exemplary methods for isolating STRO-1+ cells comprises a first step being a solid phase sorting step utilizing for example magnetic activated cell sorting (MACS) recognizing high level expression of STRO-1. A second sorting step can then follow, should that be desired, to result in a higher level of precursor cell expression as described in patent specification WO 01/14268. This second sorting step might involve the use of two or more markers.

The method obtaining STRO-1+ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1+ cell population has been obtained, it may be cultured or expanded by any suitable means to obtain MEMPs.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used to obtain the supernatant or soluble factors. In another useful example of the invention, cells of a non-human animal (or if the patient is not a human, from another species) are used to obtain supernatant or soluble factors.

The invention can be practiced using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (Gallus gallus) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present invention. In one example, the cells are maintained and stored by using cryo-preservation.

Genetically-modified Cells

In one example, the STRO-1+ cells and/or progeny cells thereof are genetically modified, e.g., to express and/or secrete a protein of interest. For example, the cells are engineered to express a protein useful in the treatment of an inflammatory joint disease, such as an anti-TNF antibody (e.g., adalimumab or infliximab) or an anti-CD20 antibody (e.g., rituximab or ocrelizumab) or a soluble TNF receptor (e.g., etanercept) or a peptide useful for treating such conditions (e.g., as described U.S. Pat. No. 5,837,686).

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present example of the invention.

For example, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present invention, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Life Technologies Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J. Virol.* 56:2731-2739 (1992); Johann et al, *J. Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl. Acad. Sci. USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) *Vaccines* 90 (Cold Spring Harbor Laboratory Press);Carter *Current Opinion in Biotechnology* 5:533-539, 1992; Muzyczka. *Current Topics in Microbiol, and Immunol.* 158:97-129, 1992; Kotin, Human Gene Therapy 5:793-801, 1994; Shelling and Smith *Gene Therapy* 7:165-169, 1994; and Zhou et al. *J. Exp. Med.* 179:1867-1875, 1994.

Additional viral vectors useful for delivering an expression construct of the invention include, for example, those derived from the pox family of viruses, such as vaccinia virus and avian poxvirus or an alphavirus or a conjugate virus vector (e.g. that described in Fisher-Hoch et al., *Proc. Natl. Acad. Sci. USA* 56:317-321, 1989).

Assaying Therapeutic/Prophylactic Potential of Cells and Soluble Factors

Methods for determining the ability of cells or soluble factors to treat or prevent or delay the onset or progression of an inflammatory joint disease will be apparent to the skilled artisan.

For example, an in vitro model of rheumatoid arthritis is described in Schultz et al., *Arthritis and Rheumatism,* 40: 1420-1428, 1997 and involves culturing synovial membranes and articular cartilage explants or synovial cells and chondrocytes from subjects suffering from arthritis in a 3-dimensional fibrin matrix. Administration of cells and or soluble factors described herein to the culture permits determining the therapeutic/prophylactic efficacy of the cells/factors, e.g., by assessing expression of proteolytic enzymes, chondrocyte matrix architecture, matrix degradation or cell numbers.

Another in vitro model of arthritis involves culturing cartilage discs with synovial fibroblasts in the presence of TNF-alpha and/or IL-1 beta. Administration of cells and or soluble factors described herein to the culture permits determining the therapeutic/prophylactic efficacy of the cells/factors, e.g., by assessing expression of proteolytic enzymes, collagen matrix architecture, matrix degradation, pro-inflammatory cytokine levels (e.g., IL-6 and/or IL-8) or cell numbers.

In another example, efficacy of cells and/or soluble factors described herein is assessed in an in vivo model of rheumatoid arthritis, e.g., a SKG strain of mouse (Sakaguchi et al., Nature, 426: 454-460), rat type II collagen arthritis model, mouse type II collagen arthritis model or antigen induced arthritis models in several species (Bendele J Musculoskel Neuron Interact 2001; 1(4):377-385). The inventors have also demonstrated a sheep model of rheumatoid arthritis.

Animal models of ankylosing spondylitis are also known in the art, and include models involving immunizing balb/c mice with aggrecan and/or versican, ank/ank mice rats overexpressing leukocyte antigen-B27.

It will be apparent to the skilled artisan from the foregoing that the present disclosure also provides a method for identifying or isolating a cell or a soluble factor for the treatment, prevention or delay of an inflammatory joint disease thereof, the method comprising:
(i) administering a cell or a soluble factor to a test subject suffering from an inflammatory joint disease and assessing inflammation in a joint of the subject;
(ii) comparing level of inflammation in the joint of the subject at (i) to the level of inflammation in the joint of a control subject suffering from the inflammatory joint disease to which the cell or soluble factor has not been administered, wherein reduced inflammation in the joint of test subject compared to the control subject indicates that the cell or soluble factor treats, prevents or delays an inflammatory joint disease.

The present disclosure also provides a method for identifying or isolating a cell or a soluble factor for the treatment, prevention or delay of an inflammatory joint disease thereof, the method comprising:
(i) contacting a test in vitro model of inflammatory joint disease and determining the level of one or more markers of inflammation in the model;
(ii) determining the level of one or more markers of inflammation in a control in vitro model of inflammatory joint disease to which the cell or soluble factor has not been administered, wherein a reduced level of the marker of inflammation in the test model compared to the control model indicates that the cell or soluble factor treats, prevents or delays an inflammatory joint disease.

Exemplary markers of inflammation include expression of proteolytic enzymes, collagen matrix architecture, matrix degradation, pro-inflammatory cytokine levels (e.g., IL-6 and/or IL-8) or inflammatory cell numbers.

The cell may be any cell described herein according to any example.

Cellular Compositions

In one example of the present disclosure STRO-1$^+$ cells and/or progeny cells thereof are administered in the form of a composition. For example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see; e.g., *Remington's Pharmaceutical Sciences*, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay inflammatory joint disease.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the invention may be produced as a liquid for direct application to the blood stream or into a tissue or a region surrounding or adjacent to a tissue, e.g., by injection.

STRO-1$^+$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the invention. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 38:145 1991; Vacanti, et al. *Plast. Reconstr. Surg.* 88:753-9 1991; or synthetic polymers such as polyanhydrides, polyorthoesters, and polylactic acid.

In another example, the cells may be administered in a gel scaffold (such as Gelfoam from Upjohn Company).

The cellular compositions useful for methods described herein may be administered alone or as admixtures with other cells. Cells that may be administered in conjunction with the compositions of the present invention include, but are not limited to, other multipotent or pluripotent cells or stem cells, or bone marrow cells. The cells of different types may be admixed with a composition of the invention immediately or shortly prior to administration, or they may be co-cultured together for a period of time prior to administration.

In one example, the composition comprises an effective amount or a therapeutically or prophylactically effective amount of cells. For example, the composition comprises about $1 \times 10^5$ STRO-1$^+$ cells/kg to about $1 \times 10^7$ STRO-1$^+$ cells/kg or about $1 \times 10^6$ STRO-1$^+$ cells/kg to about $5 \times 10^6$ STRO-1$^+$ cells/kg. The exact amount of cells to be administered is dependent upon a variety of factors, including the age, weight, and sex of the patient, and the extent and severity of the inflammatory joint disease In one example, a low dose of cells is administered to the subject. Exemplary dosages include between about $0.1 \times 10^4$ to about $0.5 \times 10^6$ cells per kg, for example, between about $0.1 \times 10^5$ to about $0.5 \times 10^6$ cells per kg, such as, between about $0.5 \times 10^5$ to about $0.5 \times 10^6$ cells per kg, for example, between about $0.1 \times 10^6$ to about $0.5 \times 10^6$ cells per kg, e.g., about $0.2 \times 10^6$ or $0.3 \times 10^6$ or $0.4 \times 10^6$ cells per kg.

In one example, a high dose of cells is administered to the subject. Exemplary dosages include at least about $1.5 \times 10^6$ cells/kg. For example, a high dose comprises between about $1.5 \times 10^6$ to about $6 \times 10^6$ cells/kg, such as between about $1.5 \times 10^6$ to about $5 \times 10^6$ cells/kg, for example, between about $1.5 \times 10^6$ to about $4 \times 10^6$ cells/kg, for example, between about $1.5 \times 10^6$ to about $3 \times 10^6$ cells/kg. For example, a high dose comprises about $1.5 \times 10^6$ or about $2 \times 10^6$ cells/kg.

In one example, the cells are administered as a total cell number dose irrespective of the patient's weight.

For example, in one example, the cells are administered at a dose of between about 100 million to 300 million cells irrespective of the weight of the patient.

For example, in one example, the cells are administered at a dose of between about 100 million to 200 million cells irrespective of the weight of the patient.

In one example, the cells are administered at a dose of about 100 million cells irrespective of the weight of the patient.

In one example, the cells are administered at a dose of about 150 million cells irrespective of the weight of the patient.

In one example, the cells are administered at a dose of about 200 million cells irrespective of the weight of the patient.

In one example, the cells are administered at a dose of about 300 million cells irrespective of the weight of the patient.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a pancreas.

In some examples of the invention, it may not be necessary or desirable to immunosuppress a patient prior to initiation of therapy with cellular compositions. Accordingly, transplantation with allogeneic, or even xenogeneic, STRO-1$^+$ cells or progeny thereof may be tolerated in some instances.

However, in other instances it may be desirable or appropriate to pharmacologically immunosuppress a patient prior to initiating cell therapy and/or reduce an immune response of a subject against the cellular composition. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. For example, the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one example of the present invention, STRO-1$^+$ cell-derived and/or progeny cell-derived supernatant or soluble factors are administered in the form of a composition, e.g., comprising a suitable carrier and/or excipient. For example, the carrier or excipient does not adversely affect the biological effect of the soluble factors or supernatant.

In one example, the composition comprises a composition of matter to stabilize a soluble factor or a component of supernatant, e.g., a protease inhibitor. For example, the protease inhibitor is not included in an amount sufficient to have an adverse effect on a subject.

Compositions comprising STRO-1$^+$ cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising STRO-1$^+$ cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof. In accordance with an alternative aspect of the invention, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be desirable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Additional Components of Compositions

The STRO-1$^+$ cell-derived supernatant or soluble factors, STRO-1$^+$ cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPDXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

In one example, the cells and/or soluble factors are administered with an immunosuppressive agent or an anti-inflammatory agent or a DMARD or a non-steroidal anti-inflammatory drug.

Exemplary immunosuppressives/anti-inflammatory agents include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077) ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine antagonists such as cytokine antibodies or cytokine receptor antibodies including anti-interferon-alpha, -beta, or -gamma antibodies, anti-tumor necrosis factor (TNF)-alpha antibodies (infliximab or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, such as anti-CD3 or anti-CD4/CD4a antibodies; soluble peptide containing a LFA-3 binding domain (WO 90/08187); streptokinase; transforming growth factor-beta (TGF-beta); streptodomase; RNA or DNA from the host; FK506; RS-61443; chlorambucil; deoxyspergualin; rapamycin; T-cell receptor (U.S. Pat. No. 5,114,721); T-cell receptor fragments (W90/11294); BAFF antagonists such as BAFF antibodies and BR3 antibodies and zTNF4 antagonists; biologic agents that interfere with T cell helper signals, such as anti-CD40 receptor or anti-CD40 ligand (CD 154), including blocking antibodies to CD40-CD40 ligand and CTLA4-Ig; and T-cell receptor antibodies (EP 340,109) such as T10B9. Some immunosuppressive agents herein are also DMARDs, such as methotrexate. Examplary immunosuppressive agents herein include cyclophosphamide, chlorambucil, azathioprine, leflunomide, MMF, or methotrexate.

Examples of "disease-modifying anti-rheumatic drugs" or "DMARDs" include hydroxycloroquine, sulfasalazine, methotrexate, leflunomide, etanercept, infliximab (plus oral and subcutaneous methotrexate), azathioprine, D-penicillamine, gold salts (oral), gold salts (intramuscular), minocycline, cyclosporine including cyclosporine A and topical cyclosporine, staphylococcal protein A, including salts and derivatives thereof, etc. In one example, the DMARD is methotrexate Examples of "non-steroidal anti-inflammatory drugs" or "NSAIDs" include aspirin, acetylsalicylic acid, ibuprofen, flurbiprofen, naproxen, indomethacin, sulindac, tolmetin, phenylbutazone, diclofenac, ketoprofen, benorylate, mefenamic acid, methotrexate, fenbufen, azapropazone; COX-2 inhibitors such as celecoxib 4-(5-(4-methylphenyl)-3-(trifluoromethyl)-1H-pyrazol-1-yl)benzenesulfonam-ide, valdecoxib, meloxicam, GR 253035 (Glaxo Wellcome); and MK966 (Merck Sharp & Dohme), including salts and derivatives thereof, etc.

Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab) or soluble TNF receptor (e.g., etanercept). Alternatively, or additionally, the other compound is a CTLA-4 antagonist (e.g., abatacept, CTLA4-Ig).

Alternatively, or additionally, the other compound is an anti-IL-6 or an anti-IL-6R antibody (e.g., tocilizumab).

In one example, the STRO-1$^+$ cells and/or progeny cells thereof and/or soluble factors derived therefrom are administered as adjunctive and/or concomitant therapy to the other therapeutic compound (e.g., methotrexate).

"Adjunctive therapy" means a treatment that is additional to or supplements a previous treatment.

"Concomitant therapy" means a treatment that is given at the same time as another treatment but is not supplemental to the other treatment, e.g., both treatments may individually treat the rheumatic disease.

Discussion herein of co-administering therapeutics or administering more than one therapeutic does not necessarily mean that the therapeutics are administered in a single composition. The therapeutics can be administered simultaneously or sequentially in separate compositions. The period between sequential administration can be several days, provided that there is still sufficient levels of the first therapeutic to provide or add to the therapeutic or prophylactic benefit of the second therapeutic when it is administered.

In one example, a pharmaceutical composition as described herein according to any example comprises a compound used to treat inflammatory joint disease. Alternatively, a method of treatment/prophylaxis as described herein according to any embodiment additionally comprises administering a compound used to treat an inflammatory joint disease (e.g., in the same composition or a separate composition and/or at the same or different time). Exemplary compounds are described herein and are to be taken to apply mutatis mutandis to these examples of the present disclosure.

In another example, a composition as described herein according to any example additionally comprises a factor that induces or enhances differentiation of a progenitor cell into a vascular cell. Exemplary factors include, vascular endothelial growth factor (VEGF), platelet derived growth factor (PDGF; e.g., PDGF-BB), and FGF.

In another example, a composition as described herein according to any example additionally comprises a tissue specific committed cell (TSCC). In this respect, International Patent Application No. PCT/AU2005/001445 demonstrates that administration of a TSCC and a STRO-1$^+$ cells can lead to enhanced proliferation of the TSCC. In one example, the TSCC is a vascular cell. Administration of such a composition to a subject may lead to increased production of vasculature, e.g., leading to increased nutrients being delivered to the affected tissue.

Medical Devices

The present disclosure also provides medical devices for use or when used in a method as described herein according to any example. For example, the present disclosure provides a syringe or catheter or other suitable delivery device comprising STRO-1$^+$ cells and/or progeny cells thereof and/or soluble factors therefrom and/or a composition as described herein according to any example. Optionally, the syringe or catheter is packaged with instructions for use in a method as described herein according to any example.

In another example, the present disclosure provides an implant comprising STRO-1$^+$ cells and/or progeny cells thereof and/or soluble factors therefrom and/or a composition as described herein according to any example. Optionally, the implant is packaged with instructions for use in a method as described herein according to any example. Suitable implants may be formed with a scaffold, e.g., as described herein above and STRO-1$^+$ cells and/or progeny cells thereof and/or soluble factors therefrom.

Modes of Administration

The STRO-1$^+$ cell-derived supernatant or soluble factors, STRO-1$^+$ cells or progeny thereof may be surgically implanted, injected, delivered (e.g., by way of a catheter or syringe), or otherwise administered directly or indirectly to the site in need of repair or augmentation, e.g., into a joint or adjacent to the joint.

In one example, the STRO-1$^+$ cell-derived supernatant or soluble factors, STRO-1$^+$ cells or progeny thereof is/are delivered to the blood stream of a subject. For example, the STRO-1$^+$ cell-derived supernatant or soluble factors, STRO-1$^+$ cells or progeny thereof are delivered parenterally. Exemplary routes of parenteral administration include, but are not limited to, intraperitoneal, intraventricular, intracerebroventricular, intrathecal, intra-arterial, intranodal or intravenous. In one example, the STRO-1$^+$ cell-derived supernatant or soluble factors, STRO-1$^+$ cells or progeny thereof are delivered intra-arterially, into an aorta, into an atrium or ventricle of the heart or into a blood vessel, e.g., intravenously.

In the case of cell delivery to an atrium or ventricle of the heart, cells can be administered to the left atrium or ventricle to avoid complications that may arise from rapid delivery of cells to the lungs.

In one example, the STRO-1$^+$ cell-derived supernatant or soluble factors, STRO-1$^+$ cells or progeny thereof are injected into the site of delivery, e.g., using a syringe or through a catheter or a central line.

Selecting an administration regimen for a therapeutic formulation depends on several factors, including the serum or tissue turnover rate of the entity, the level of symptoms, and the immunogenicity of the entity. For example, an administration regimen maximizes the amount of therapeutic compound delivered to the patient consistent with an acceptable level of side effects. Accordingly, the amount of formulation delivered depends in part on the particular entity and the severity of the condition being treated.

In one example, STRO-1$^+$ cell-derived supernatant or soluble factors, STRO-1$^+$ cells or progeny thereof are delivered as a single bolus dose. Alternatively, STRO-1$^+$ cell-derived supernatant or soluble factors, STRO-1$^+$ cells or progeny thereof are administered by continuous infusion, or by doses at intervals of, e.g., one day, one week, or 1-7 times per week. An exemplary dose protocol is one involving the maximal dose or dose frequency that avoids significant undesirable side effects. A total weekly dose depends on the type and activity of the compound being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects. Important diagnostic measures include those of symptoms of diabetes.

The present inventors have shown therapeutic benefits provided by STRO-1$^+$ cells and/or progeny thereof and/or soluble factors derived therefrom are observed for at least four weeks in a subject. Accordingly, in some examples the cells are administered weekly, fortnightly, once every three weeks or once every four weeks.

In accordance with examples of the invention directed to treating or delaying the progression of an inflammatory joint disease, in one example, the STRO-1$^+$ cells and/or progeny cells thereof and/or soluble factors derived therefrom are administered following diagnosis of the disorder, e.g., using standard methods known in the art and/or described herein.

For those examples directed to preventing or delaying the onset of an inflammatory joint disease, the STRO-1$^+$ cells and/or progeny cells thereof and/or soluble factors derived therefrom can be administered prior to clinical diagnosis of the disorder.

Patient Populations

The methods of present disclosure are also useful for treating subjects falling within sub-populations of subjects suffering from a rheumatic disease.

In one example, the subject suffers from rheumatic disease, e.g., rheumatoid arthritis, and does not respond adequately to a TNF inhibitor (e.g., an anti-TNF antibody or a soluble TNF receptor). A subject who "does not respond adequately to a TNF inhibitor" has experienced an inadequate response to previous or current treatment with one or more TNF inhibitors because of toxicity or inadequate efficacy. In one example, such patient has received, for example, etanercept for >3 months at 25 mg twice a week or at least 4 infusions of infliximab at >3 mg/kg but has had an inadequate response thereto.

In one example, the subject suffers from rheumatic disease, e.g., rheumatoid arthritis, and does not respond adequately to methotrexate. A subject who "does not respond adequately to methotrexate" is a patient who has experienced an inadequate response to previous or current treatment with methotrexate because of toxicity or inadequate efficacy. In one example, the patient has been on methotrexate (10-25 mg/week) for at least 12 weeks and still has active disease.

In one example, the subject is already receiving treatment with methotrexate.

In one example, the subject is already receiving treatment with methotrexate and administration of the STRO-1$^+$ cells and/or progeny cells thereof and/or soluble factors derived therefrom delays prescription of an anti-TNF therapy compared to a subject who has not received the STRO-1$^+$ cells and/or progeny cells thereof and/or soluble factors derived therefrom.

In one example, the subject suffers from active rheumatoid arthritis. A subject with "active rheumatoid arthritis" means a subject with active and not latent symptoms of rheumatoid arthritis. In one example, such patient has moderate-to-severe active rheumatoid arthritis of >6 months disease duration at time of baseline visit. In one example, such patients will have: (1) swollen joint count (SJC)>4 (66 joint count), (2) tender joint count (TJC)>4 (68 joint count), and/or C-reactive protein (CRP)>upper limit of normal (ULN) at screening visit.

In one example, the subject suffers from moderate active rheumatoid arthritis or severe active rheumatoid arthritis or moderate to severe active rheumatoid arthritis.

A person having moderate active rheumatoid arthritis generally has a combination of at least two or three or four or all of the following symptoms:

Between 6 and 20 inflamed joints
Usually no inflammation in tissues other than the joints
An elevated ESR or CRP levels
A positive rheumatoid factor test or anti-cyclic citrullinated peptide (anti-CCP) antibodies
Evidence of inflammation but no evidence of bone datnage on x-rays A person having severe active rheumatoid arthritis generally has a combination of at least two or three or four or all of the following symptoms:

More than 20 persistently inflamed joints or a rapid loss of functional abilities
Elevated ESR or CRP levels
Anemia related to chronic illness
Low blood albumin level
A positive rheumatoid factor test, often with a high level
Evidence of bone and cartilage damage on x-ray
Inflammation in tissues other than joints In one example, a subject has persistently active rheumatoid arthritis. A person with persistently active rheumatoid arthritis has had evidence of inflammation for at least six to twelve months and may have irreversible joint damage and loss of function.

In one example, administration of the cells or soluble factors inhibits progression of structural joint damage. The expression "inhibiting progression of structural joint damage" in a subject refers to preventing or slowing structural joint damage caused by a rheumatic disease, e.g., a subject suffering from rheumatoid arthritis for example based on eroded joint count and/or joint damage score. Methods for measuring progression of structural joint damage are known to the skilled person, and include, without limitation Genant-modified Total Sharp Score (TSS), erosion score (ES), and/or joint space narrowing (JSN) score. In one example, a method disclosed herein additionally comprises assessing progression of structural joint damage, e.g., using a method described herein and/or by X-ray. For example, the assessment is made about 1 month or 3 months or 6 months or 12 months after the last administration of the cells or soluble factors.

The present invention is described further in the following non-limiting examples.

EXAMPLES

Example 1

Immunoselection of MPCs by Selection of STRO-3+ Cells

Bone marrow (BM) is harvested from healthy normal adult volunteers (20-35 years old). Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino, A. C. et al. (1998) Blood 92: 2613-2628). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3+ (or TNAP+) cells were subsequently isolated by magnetic activated cell sorting as previously described (Gronthos et al. (2003) Journal of Cell Science 116: 1827-1835; Gronthos, S, and Simmons, P. J. (1995) Blood 85: 929-940). Briefly, approximately $1-3\times10^8$ BMMNC are incubated in blocking buffer, consisting of 10% (v/v) normal rabbit serum in HHF for 20 minutes on ice. The cells are incubated with 200 µl of a 10 µg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred µl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP+ cells are isolated by positive pressure. An aliquot of cells from each fraction can be stained with streptavidin-FITC and the purity assessed by flow cytometry.

Example 2

Cells Selected by STRO-3 mAb are STRO-1$^{bright}$ Cells

Experiments were designed to confirm the potential of using. STRO-3 mAb as a single reagent for isolating cells STRO-1$^{bright}$ cells.

Given that STRO-3 (IgG1) is a different isotype to that of STRO-1 (IgM), the ability of STRO-3 to identify clonogenic CFU-F was assessed by two-color FACS analysis based on its co-expression with STRO-1+ cells isolated using the MACS procedure (FIG. 1). The dot plot histogram represents $5\times10^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1+ cells failed to react with the STRO-3 mAb. Cells isolated by FACS from all four quadrants were subsequently assayed for the incidence of CFU-F (Table 1).

TABLE 1

Enrichment of human bone marrow cells by dual-colour FACS analysis based on the co-expression of the cell surface markers STRO-1 and TNAP (refer to FIG. 1). FACS sorted cells were cultured under standard clonogenic conditions in alpha MEM supplemented with 20% FCS. The data represents the mean number of day 14 colony-forming cells (CFU-F) per $10^5$ cells plated ± SE (n = 3 different bone marrow aspirates). These data suggest that human MPC are exclusively restricted to the TNAP positive fraction of BM which co-express the STRO-1 antigen brightly.

| Bone Marrow Fraction | Frequency of CFU-F/$10^5$ Cells | Enrichment (Fold Increase) |
|---|---|---|
| Unfractionated BMMNC | 11.0 ± 2.2 | 1.0 |
| TNAP+/STRO-1$^{bright}$ | 4,511 ± 185 | 410 |
| TNAP+/STRO-1$^{dull}$ | 0.0 | 0.0 |

Example 3

Figure 2:
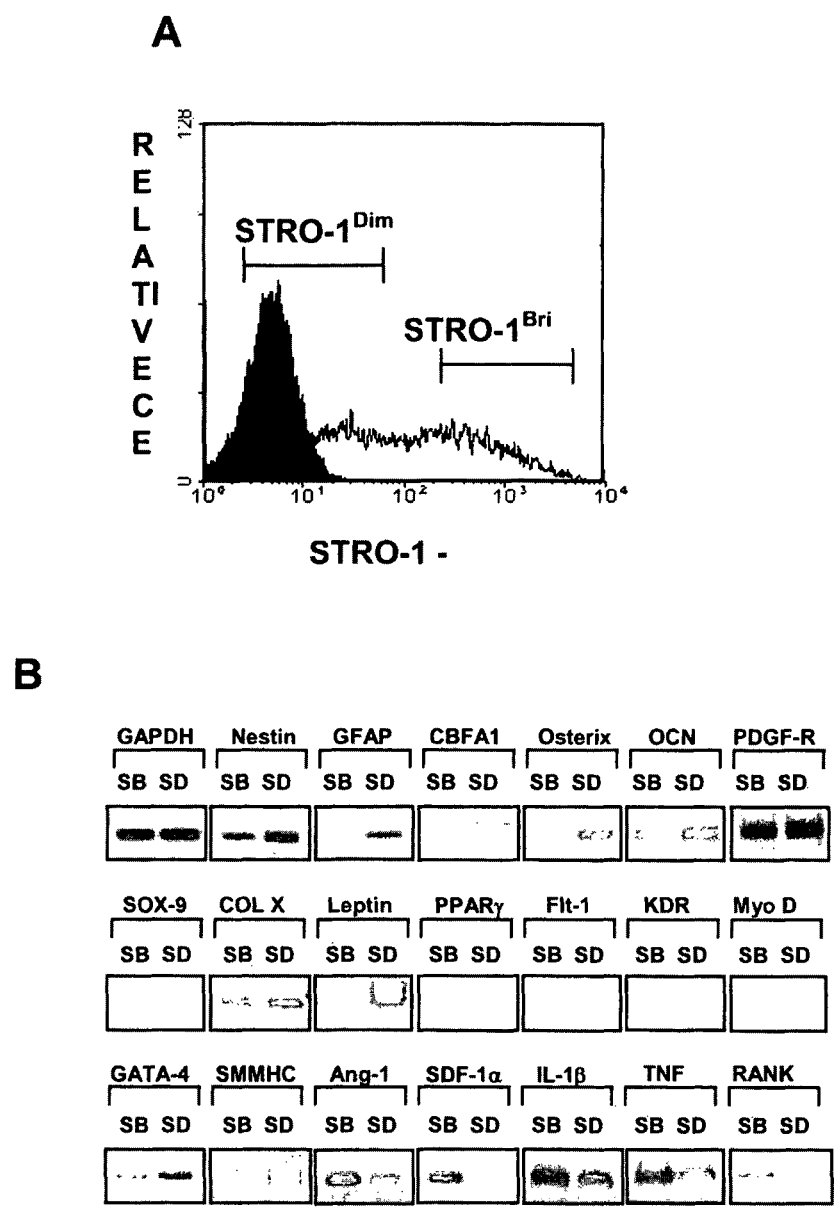
FIG. 2. Gene expression profile of STRO-1$^{bright}$ or STRO-1$^{dim}$ progeny of cultured and expanded STRO-1$^{bright}$ MPC. Single cell suspensions of ex vivo expanded bone marrow MPC were prepared by trypsin/EDTA treatment. Cells were stained with the STRO-1 antibody which was subsequently revealed by incubation with goat-anti murine IgM-fluorescein isothiocyanate. Total cellular RNA was prepared from purified populations of STRO-1$^{dim}$ or STRO-1$^{bright}$ expressing cells, following fluorescence activated cell sorting (A). Using RNAzolB extraction method, and standard procedures, total RNA was isolated from each subpopulation and used as a template for cDNA synthesis. The expression of various transcripts was assessed by PCR amplification, using a standard protocol as described previously (Gronthos et al. *J Cell Sci.* 116:1827-1835, 2003). Primers sets used in this study are shown in Table 2. Following amplification, each reaction mixture was analyzed by 1.5% agarose gel electrophoresis, and visualized by ethidium bromide staining (B). Relative gene expression for each cell marker was assessed with reference to the expression of the house-keeping gene, GAPDH, using ImageQant software (C).
Figure 2:
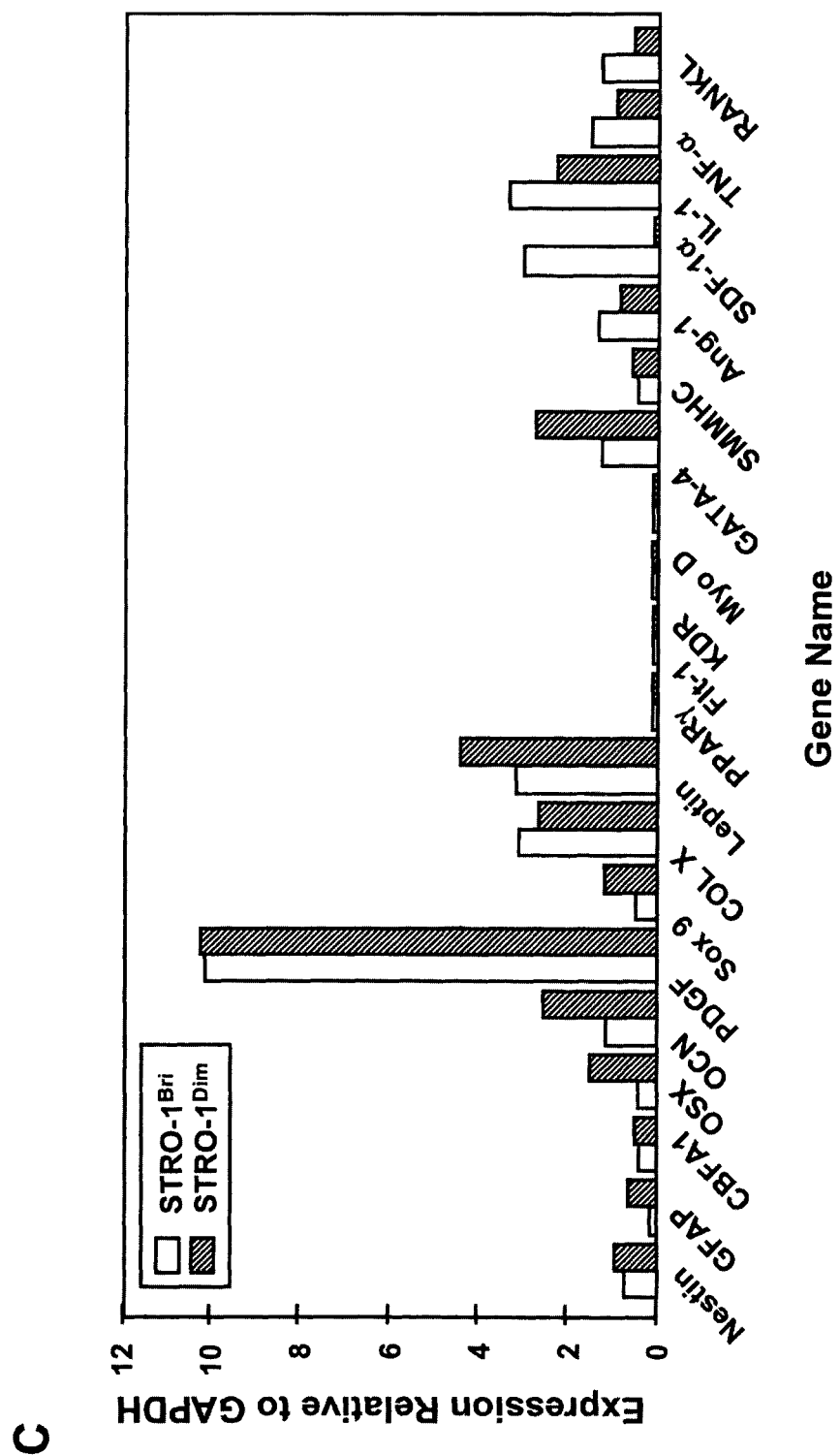

Relative Gene and Surface Protein Expression of STRO-1$^{dull}$ and STRO-1$^{bright}$ Cells In the first series of experiments, semi-quantitative RT-PCR analysis was employed to examine the gene expression profile of various lineage-associated genes expressed by STRO-1$^{dull}$ or STRO-1$^{bright}$ populations, isolated by fluorescence activated cell sorting (FIG. 2A). In the second series of experiments, flow cytometry and mean channel fluorescence analysis was employed to examine the surface protein expression profile of various lineage-associated proteins expressed by STRO-1$^{dull}$ or STRO-1$^{bright}$ populations, isolated by fluorescence activated cell sorting.

Total cellular RNA was prepared from either $2\times10^6$ STRO-1$^{bright}$ or STRO-1$^{dull}$ sorted primary cells, chondrocyte pellets and other induced cultures and lysed using RNAzolB extraction method (Biotecx Lab. Inc., Houston, Tex.), according to the manufacturer's recommendations. RNA isolated from each subpopulation was then used as a template. for cDNA synthesis, prepared using a First-strand cDNA synthesis kit (Pharmacia Biotech, Uppsala, Sweden). The expression of various transcripts was assessed by PCR amplification, using a standard protocol as described previously (Gronthos et al., J. Bone and Min. Res. 14:48-57, 1999). Primer sets used in this study are shown in Table 2. Following amplification, each reaction mixture was analyzed by 1.5% agarose gel electrophoresis, and visualized by ethidium bromide staining. RNA integrity was assessed by the expression of GAPDH.

Relative gene expression for each cell marker was assessed with reference to the expression of the house-keeping gene, GAPDH, using ImageQant software (FIG. 2B, C). In addition, dual-colour flow cytometric analysis was used to examine the protein expression profile of ex vivo expanded MPC based on their expression of a wider range of cell lineage-associated markers in combination with the STRO-1 antibody. A summary of the general phenotype based on the gene and protein expression of STRO-1$^{dull}$ and STRO-1$^{bri}$ cultured cells is presented in Table 3. The data indicate that ex vivo expanded STRO-1$^{bright}$ MPC exhibit differentially higher expression of markers associated with perivascular cells, including angiopoietin-1, VCAM-1, SDF-1, IL-1$_\beta$, TNF$\alpha$, and RANKL. Comparisons between the protein and gene expression profiles of STRO-1$^{dull}$ and STRO-1$^{bright}$ cultured cells are summarized in Tables 3 and 4.

Subtractive hybridization studies were also performed in order to identify genes uniquely expressed by STRO-1$^{bri}$ cells. Briefly, STRO-1$^{dull}$ and STRO-1$^{bright}$ were isolated as described above (see FIG. 3A). Total RNA was prepared from STRO-1$^{dull}$ and STRO-1$^{bright}$ cells pooled from 5 different marrow samples using the RNA STAT-60 system (TEL-TEST). First-strand synthesize was performed using the SMART cDNA synthesis kit (Clontech Laboratories). The resultant mRNA/single-stranded cDNA hybrid was amplified by long-distance PCR (Advantage 2 PCR kit; Clontech) using specific primer sites at the 3' and 5' prime ends formed during the initial RT process according to the manufacturer's specifications. Following RsaI digestion of the STRO-1$^{bright}$ cDNA, 2 aliquots were used to ligate different specific adaptor oligonucleotides using the Clontech PCR-Select cDNA Subtraction Kit. Two rounds of subtractive hybridization were performed using STRO-1$^{bright}$ (tester) and STRO-1$^{dull}$ (driver) cDNA, and vice versa, according to the manufacturer's protocol. This procedure was also performed in reverse using STRO-1$_{dull}$ tester cDNA hybridized against STRO-1$^{bright}$ driver cDNA.

Figure 3:
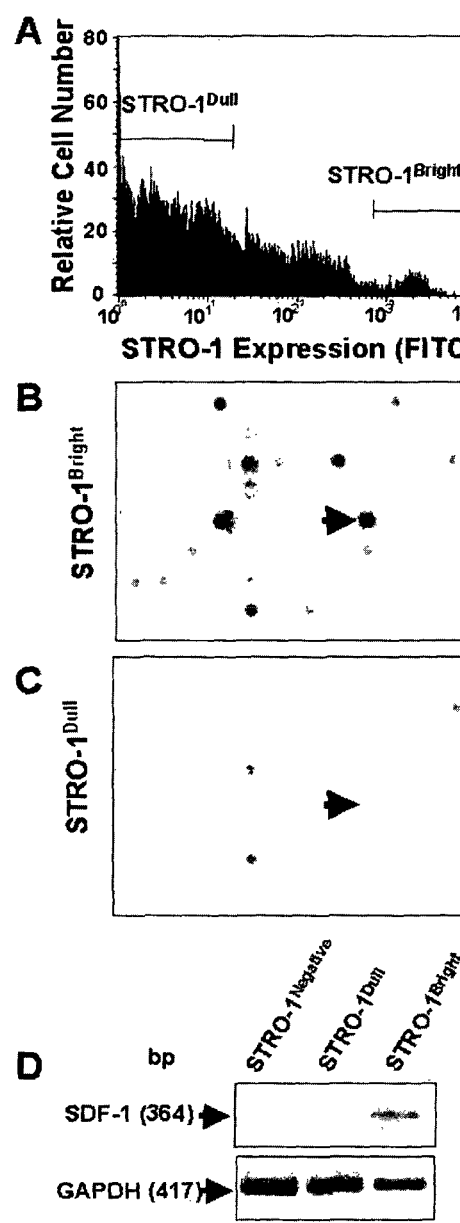
FIG. 3. STRO-1$^{bright}$ progeny of cultured and expanded STRO-1$^+$ MPC express high levels of SDF-1, STRO-1$^{dim}$ progeny do not. (A) MACS-isolated preparations of STRO-1$^+$ BMMNCs were partitioned into different STRO-1 subsets according to the regions, STRO-1$^{bright}$ and STRO-1$^{dim/dull}$ using FACS. Total RNA was prepared from each STRO-1 subpopulation and used to construct a STRO-1$^{bright}$ subtraction hybridization library (B-C). Replicate nitrocellulose filters, which have been blotted with representative PCR products amplified from bacterial clones transformed with STRO-1$^{bright}$ subtracted cDNA. The filters were then probed with either [$^{32}$P] deoxycytidine triphosphate (dCTP)-labeled STRO-1$^{bright}$ (B) or STRO-1$^{dim/dull}$ (C) subtracted cDNA. The arrows indicate differential expression of 1 clone containing a cDNA fragment corresponding to human SDF-1. (D) Reverse transcriptase (RT)-PCR analysis demonstrating the relative expression of SDF-1 and glyceraldehyde-3-phosphate dehydrogenase (GAPDH) transcripts in total RNA prepared from freshly MACS/FACS-isolated BMMNC STRO-1 populations prior to culture. bp indicates base pair.

To identify genes uniquely expressed by STRO-1$^{bright}$ population, STRO-1$^{bright}$-subtracted cDNA was used to construct replicate low-density microarray filters comprising 200 randomly selected bacterial clones transformed with the STRO-1$^{bright}$ subtracted cDNAs ligated into a T/A cloning vector. The miiroarrays were subsequently probed with either [$^{32}$P] dCTP-labeled STRO-1$^{bright}$ or STRO-1$^{dull}$ subtracted cDNA (FIG. 3B-C). Differential screening identified a total of 44 clones, which were highly differentially expressed between the STRO-1$^{dull}$ and STRO-1$^{bright}$ subpopulations. DNA sequencing of all the differentially expressed clones revealed that only 1 clone was representative of a known stromal cell mitogen; namely, platelet-derived growth factor (PDGF) (Gronthos and Simmons, *Blood.* 85: 929-940, 1995). Interestingly, 6 of the 44 clones were found to contain DNA inserts corresponding to the chemokine, stromal-derived factor-1 (SDF-1). The high abundance of SDF-1 transcripts in human STRO-1$^{bright}$ cells was confirmed by semiquantitative RT-PCR of total RNA prepared from freshly sorted STRO-1$^{bright}$, STRO-1$^{dull}$, and STRO-1$^{negative}$ bone marrow subpopulations (FIG. 3D and Table 3).

TABLE 2

RT-PCR primers and conditions for the specific amplification of human mRNA

| Target Gene | Sense/Antisense (5'-3') Primer Sequences | Product Size |
|---|---|---|
| GAPDH | CACTGACACGTTGGCAGTGG (SEQ ID NO: 1) CATGGAGAAGGCTGGGGCTC (SEQ ID NO: 2) | 417 |
| SDF-1 | GAGACCCGCGCTCGTCCGCC (SEQ ID NO: 3) GCTGGACTCCTACTGTAAGGG (SEQ ID NO: 4) | 364 |

TABLE 2-continued

RT-PCR primers and conditions for the specific amplification of human mRNA

| Target Gene | Sense/Antisense (5'-3') Primer Sequences | Product Size |
|---|---|---|
| IL-1β | AGGAAGATGCTGGTTCCCTCTC (SEQ ID NO: 5) CAGTTCAGTGATCGTACAGGTGC (SEQ ID NO: 6) | 151 |
| LT-1 | TCACTATGGAAGATCTGATTTCTTACAGT (SEQ ID NO: 7) GGTATAAATACACATGTGCTTCTAG (SEQ ID NO: 8) | 380 |
| TNF-α | TCAGATCATCTTCTCGAACC (SEQ ID NO: 9) CAGATAGATGGGCTCATACC (SEQ ID NO: 10) | 361 |
| KDR | TATAGATGGTGTAACCCGGA (SEQ ID NO: 11) TTTGTCACTGAGACAGCTTGG (SEQ ID NO: 12) | 450 |
| RANKL | AACAGGCCTTTCAAGGAGCTG (SEQ ID NO: 13) TAAGGAGGGGTTGGAGACCTCG (SEQ ID NO: 14) | 538 |
| Leptin | ATGCATTGGGAACCCTGTGC (SEQ ID NO: 15) GCACCCAGGGCTGAGGTCCA (SEQ ID NO: 16) | 492 |
| CBFA-1 | GTGGACGAGGCAAGAGTTTCA (SEQ ID NO: 17) TGGCAGGTAGGTGTGGTAGTG (SEQ ID NO: 18) | 632 |
| PPARγ2 | AACTGCGGGGAAACTTGGGAGATTCTCC (SEQ ID NO: 18) AATAATAAGGTGGAGATGCAGGCTCC (SEQ ID NO: 19) | 341 |
| OCN | ATGAGAGCCCTCACACTCCTC (SEQ ID NO: 20) CGTAGAAGCGCCGATAGGC (SEQ ID NO: 21) | 289 |
| MyoD | AAGCGCCATCTCTTGAGGTA (SEQ ID NO: 22) GCGAGAAACGTGAACCTAGC (SEQ ID NO: 23) | 270 |
| SMMHC | CTGGGCAACGTAGTAAAACC (SEQ ID NO: 24) TATAGCTCATTGCAGCCTCG (SEQ ID NO: 25) | 150 |
| GFAP | CTGTTGCCAGAGATGGAGGTT (SEQ ID NO: 26) TCATCGCTCAGGAGGTCCTT (SEQ ID NO: 27) | 370 |
| Nestin | GGCAGCGTTGGAACAGAGGTTGGA (SEQ ID NO: 28) CTCTAAACTGGAGTGGTCAGGGCT (SEQ ID NO: 29) | 460 |
| SOX9 | CTCTGCCTGTTTGGACTTTGT (SEQ ID NO: 30) CCTTTGCTTGCCTTTTACCTC (SEQ ID NO: 31) | 598 |

TABLE 2-continued

RT-PCR primers and conditions for the specific amplification of human mRNA

| Target Gene | Sense/Antisense (5'-3') Primer Sequences | Product Size |
|---|---|---|
| Collagen type X | AGCCAGGGTTGCCAGGACCA (SEQ ID NO: 32) TTTTCCCACTCCAGGAGGGC (SEQ ID NO: 33) | 387 |
| Aggrecan | CACTGTTACCGCCACTTCCC (SEQ ID NO: 34) ACCAGCGGAAGTCCCCTTCG (SEQ ID NO: 35) | 184 |

TABLE 3

Summary of the Relative Gene Expression in STRO-1$^{Bright}$ and STRO-1$^{Dull}$ populations. A list of genes which displayed measurable and differential expression between the STRO-1$^{Bright}$ and STRO-1$^{Dull}$ populations as determined by reverse transcription-PCR are presented. Values represent the relative gene expression with reference to the house-keeping gene, GAPDH.

| | | Gene Expression relative to GAPDH | |
|---|---|---|---|
| Tissue | Marker | STRO-1$^{Bright}$ | STRO-1$^{Dull}$ |
| Neurons | GFAP (Glial Fibrillary Acidic Protein) | 0.1 | 0.7 |
| Bone | OCN (Osteocalcin) | 1.1 | 2.5 |
| | OSX (Osterix) | 0.4 | 1.3 |
| | CBFA-1 (Core Factor Binding Protein-1) | 0.3 | 0.6 |
| Immuno-regulatory | RANKL (Receptor Activator of Nuclear Factor κ B) | 1.6 | 0.3 |
| | SDF-1-alpha (Stromal Derived factor-1-alpha) | 3.2 | 0.1 |
| Fat | Leptin | 3.1 | 4.2 |
| Cardiomyocytes | GATA-4 | 1.1 | 2.9 |
| Endothelial cells | Ang-1 (Angiopoietin-1) | 1.5 | 0.8 |
| Chondrocytes | Sox 9 | 0.3 | 1.1 |
| | COL X (Collagen X) | 3.5 | 2.8 |
| Pro-inflammatory Cytokines | TNF-alpha (Tumor necrosis alpha) | 1.7 | 0.9 |

To correlate protein surface expression with density of STRO-1 expression, single cell suspensions of ex vivo expanded cells derived bone marrow MPC were prepared by trypsin/EDTA detachment and subsequently incubated with the STRO-1 antibody in combination with antibodies identifying a wide range of cell lineage-associated markers. STRO-1 was identified using a goat anti-murine IgM-fluorescein isothiocyanate while all other markers were identified using either a goat anti-mouse or anti-rabbit IgG-phycoerythrin. For those antibodies identifying intracellular antigens, cell preparations were first labeled with the STRO-1 antibody, fixed with cold 70% ethanol to permeabilize the cellular membrane and then incubated with intracellular antigen-specific antibodies. Isotype matched control antibodies were used under identical conditions. Dual-colour flow cytometric analysis was performed using a COULTER EPICS flow cytometer and list mode data collected. The dot plots represent 5,000 listmode events indicating the level of fluorescence intensity for each lineage cell marker (y-axis) and STRO-1 (x-axis). The vertical and horizontal quadrants were established with reference to the isotype matched negative control antibodies.

TABLE 4

Summary of the Relative Protein Expression in STRO-1$^{Bright}$ and STRO-1$^{Dull}$ populations. A list of proteins which displayed differential expression between the STRO-1$^{Bri}$ and STRO-1$^{Dull}$ populations as determined by flow cytometry are presented. Values represent the relative mean fluorescence intensity of staining.

| | | Mean Fluorescence Intensity | |
|---|---|---|---|
| Tissue | Marker | STRO-1$^{Bright}$ | STRO-1$^{Dull}$ |
| Neurons | Neurofilament | 1.7 | 20.5 |
| Bone | ALK PHOS (Alkaline Phophatase) | 5.7 | 44.5 |
| Immunoregulatory | RANKL (Receptor Activator of Nuclear Factor κ B) | 658.5 | 31.0 |
| Epithelial Cells | CytoKeratin 10 + 13 | 1.2 | 23.3 |
| | Cytokeratin 14 | 1.8 | 8.8 |
| Smooth Muscle | α-SMA (Alpha Smooth Muscle Actin) | 318.0 | 286.0 |
| Chondrocytes | Byglycan | 84.4 | 65.9 |
| Basal Fibroblast | Tenascin C | 22.2 | 6.9 |
| Cardiomyocyte | Troponin C | 2.5 | 15.0 |

Example 4

A Sheep Model of Rheumatoid Arthritis

4.1 Methods

An outline of the method for producing a sheep model of rheumatoid arthritis is as follows:

1. Day 0
   i. 5 sheep (B1626, B1584, B3619, B1612, B1302) were administered Freund's complete adjuvant+5 mg Bovine type II collagen (5×0.2 ml S/C per sheep). Solution was administered subcutaneously (S/C)
   ii. 2 sheep (B1627, B4036) were administered Freund's complete adjuvant+5 mg Chicken type II collagen (5×0.2 ml S/C per sheep)
   iii. 10 ml of blood was collected for testing for Collagen type II antibodies using an ELISA
   iv. Clinical examination for the following:
      © Lameness
      © Swelling
      © Joint thickening
2. Day 14
   i. 5 sheep were administered Freund's incomplete adjuvant+5 mg Bovine type II collagen (5×0.2 ml S/C per sheep)
   ii. 2 sheep were administered Freund's incomplete adjuvant+5 mg Chicken II collagen (5×0.2 ml S/C per sheep)
   iii. 10 ml of blood was collected for testing for Collagen type II antibodies using an ELISA and white blood cell counts
   iv. Clinical examination for the following:
      © Lameness
      © Swelling
      © Joint thickening
3. Day 28
   i. 5 sheep were administered 100 μg bovine type II collagen in saline via intra-articular injection into left hock (500 μl per sheep)
   ii. 2 sheep 100 μg chicken type II collagen intra-articular injection in saline into left hock (500 μl per sheep)
   iii. 10 ml of blood was collected for testing for Collagen type II antibodies using an ELISA and white blood cell counts
   iv. Clinical examination for the following:
      © Lameness
      © Swelling
      © Joint thickening
4. Day 30 +2 days IA injection
   i. Clinical examination for the following:
      © Lameness
      © Swelling
      © Joint thickening
5. Day 36 +8 days IA injection
   i. Clinical examination for the following:
      © Lameness
      © Swelling
      © Joint thickening
6. Day 42+14 days IA injection
   i. 4 sheep (B1626, B3619, B1612, B1302) receiving the bovine type II collagen were killed
   ii. 2 sheep (B1627, B4036) receiving the chicken type II collagen were killed
   iii. 10 ml of blood was collected for testing for Collagen type II antibodies using an ELISA and white blood cell counts
   iv. Clinical examination for the following:
      © Lameness
      © Swelling
      © Joint thickening
   v. Killed sheep
      © Synovial fluid left & right hock joints
         a. Assessed for collagen type II antibodies
         b. Cell counts
      © Synovial tissue left & right hock joints
         a. Formalin fixation. H&E sections
         b. Liquid nitrogen freezing
      © Articular Cartilage left and right
         a. Photos
         b. Formalin fixation and de-calcification for H & E
7. Day 56
   i. 1 sheep (1584) receiving bovine collagen type II killed
   ii. 10 ml of blood was collected for testing for Collagen type II antibodies using an ELISA and white blood cell counts
   iii. Clinical examination for the following
      © Lameness
      © Swelling
      © Joint thickening
   iv. Killed sheep
      © Synovial fluid left & right hock joints
         a. Assessed for collagen type II antibodies Cell counts
      © Synovial tissue left & right hock joints
         a. Formalin fixation H&E sections
         b. Liquid nitrogen freezing
      © Articular Cartilage L & R
         a. Photos
         b. Formalin fixation and de-calcification for H & E

4.2 Results

Clinical signs of mild lameness were evident in all 7 sheep, with joint swelling and pain on joint flexion apparent in 4 sheep. These signs were observed in the left (treated) hock only.

After the sheep were euthanased, gross thickening of the synovium surrounding the tibiotarsal joint was evident in 6 of the 7 sheep. This was the most striking evidence of inflammatory changes. Examining the articular cartilage of this joint, gross inflammatory erosive lesions were observed in 3 of the sheep, most notably on the articular surface of the talus bone.

Where inflammatory changes were observed in the left (treated) hock, in the contralateral (right) hock very mild inflammatory changes were occasionally observed.

Table 5 summarizes results of features observed in treated sheep.

TABLE 5

Summary of the clinical, gross pathological and histopathological features observed in the 7 sheep

| | Sheep | | | | | | |
|---|---|---|---|---|---|---|---|
| | B1626 | B1584 | B1627 | B4036 | B3619 | B1612 | B1302 |
| Treatment | BCII | BCII | CCII | CCII | BCII | BCII | BCII |
| Length of treatment | 42 d | 56 d | 42 d | 42 d | 42 d | 42 d | 42 d |

TABLE 5-continued

Summary of the clinical, gross pathological and histopathological features observed in the 7 sheep

| | Sheep | | | | | | |
|---|---|---|---|---|---|---|---|
| | B1626 | B1584 | B1627 | B4036 | B3619 | B1612 | B1302 |
| Clinical Assesment | | | | | | | |
| Lameness | ++ | + | ++ | + | ++ | ++ | + |
| Joint swelling | + | 0 | ++ | 0 | ++ | ++ | 0 |
| Pain on flexion | + | 0 | + | 0 | + | + | 0 |
| Necropsy Synovium | +<br>Thickening | +<br>Thickening | ++ Thickening | Thickening | ++<br>Thickening | ++<br>Thickening | −<br>Normal |
| Articular Cartilage | No gross lesions | No gross lesions | Cartilage lesion | No gross lesions | Cartilage lesion | Cartilage lesion | No gross lesions |
| Histopathology Synovitis grading/9 (see Table 7) | 5 | 3 | 6 | 6 | 9 | 9 | 4 |
| Synovium | Synovial membrane moderately thickened. Marked inflammatory cell infiltrate, lymphocytes and plasma cells. | Early signs of inflammation, including perivascular lymphocytes. Synovial membrane is slightly thickened | Marked stromal thickening and fibrosis, increased vascularity Synovial membrane thickened. lymphocytic perivascular infiltrate. | Fibrin/collagen? deposition in synovium, many fibroblasts. Perivascular leukocyte aggregates, with lymphocytes and plasma cells. | Synovial membrane thickening and fibrosis. Stromal fibrosis and perivascular lymphocyte accumulation | Synovial membrane markedly thickened by fibrosis. Marked cellular infiltrate in stroma and some areas of necrosis. | Mild synovial thickening and fibrosis. |
| Articular Cartilage | No cartilage lesions evident on section | No cartilage lesions evident on section | Full thickness erosion and inflammation | No cartilage lesions evident on section | Full thickness erosions and also partial thickness inflamed areas | Full thickness inflammatory erosion, lymphocytes and macrophages | No cartilage lesions evident on section |

Clinical Assessments of Sheep
Table 6 sets out the scoring system used to assess treated sheep.

TABLE 6

Clinical scoring

| Lameness | | | |
|---|---|---|---|
| Score | Behaviour | Standing posture | Gait |
| 0 | Behaviour unaffected | Sheep stands squarely on all 4 legs | Even strides; able to change direction rapidly |
| 1 | | Sheep stands squarely on all 4 legs | Abnormal stride length (not easily identified). Movement no longer fluent. Still able to change direction easily. |
| 2 | | Uneven posture | Shortened stride. Lameness detected in a straight line. Awkward changing direction |
| 3 | | Uneven posture. Sheep will not bear weight on affected limb. | Shortened stride. Minimum weight bearing on affected limb |
| 4 | Will try to remain separate from others in the group | Affected limb elevated off floor | Sheep may not place affected limb to the ground when moving |
| 5 | | Will not stand unaided | Does not move. |

| Score | Joint swelling | Joint pain on flexion |
|---|---|---|
| 0 | None detectable | None elicited |
| 1 | Barely detectable but present | Slight discomfort on strong flexion |
| 2 | Clearly discernible swelling on palpation | Clear discomfort with strong flexion |
| 3 | Very marked joint swelling | Severe discomfort even with slight flexion; sheep very reluctant to flex joint |

Tables 7-11 show results of clinical assessment of sheep at various timepoints. No clinical changes observed until after IA injection of CII.

TABLE 7

Clinical assessment (+2 d IA)

| | 1626 BII | 1584 BII | 1627 CII | 4036 CII | 3619 BII | 1612 BII | 1302 BII |
|---|---|---|---|---|---|---|---|
| Lameness | 1/5 | 2/5 | 3/5 | 3/5 | 2/5 | 3/5 | 2/5 |
| Joint swelling | 0/3 | 0/3 | 1/3 | 1/3 | 1/3 | 2/3 | 0/3 |
| Joint pain on flexion | 0/3 | 0/3 | 2/3 | 2/3 | 2/3 | 2/3 | 2/3 |
| Other | — | Stiff slight | Heat | heat | Less Heat | Heat | -heat |

TABLE 8

Clinical assessment (+8 d IA)

| | 1626 BII | 1584 BII | 1627 CII | 4036 CII | 3619 BII | 1612 BII | 1302 BII |
|---|---|---|---|---|---|---|---|
| Lameness | 1/5 | 1/5 | 2/5 | 1/5 | 0/5 | 1/5 | 0/5 |
| Joint swelling | 1/3 | 0/3 | 1/3 | 1/3 | 0/3 | 1/3 | 1/3 |
| Joint pain on flexion | 1/3 | 1/3 | 2/3 | 1/3 | 0/3 | 1/3 | 0/3 |
| Other | Slight heat | Heat | Heat | Slight heat | — | Heat | Slight heat |

TABLE 9

Clinical assessment (+14 d IA)

| | 1626 BII | 1584 BII | 1627 CII | 4036 CII | 3619 BII | 1612 BII | 1302 BII |
|---|---|---|---|---|---|---|---|
| Lameness | 2/5 | 1/5 | 2/5 | 1/5 | 2/5 | 2/5 | 1/5 |
| Joint swelling | 1/3 | 0/3 | 2/3 | 0/3 | 2/3 | 2/3 | 0/3 |
| Joint pain on flexion | 1/3 | 0/3 | 1/3 | 0/3 | 1/3 | 1/3 | 0/30 |
| Necropsy Results synovium | Slightly thickened + | Ongoing | Synovial thickening ++ | slight thickening + | Synovial thickening ++ | Synovial thickening ++ | Normal gross appearance |
| Articular cartilage | No gross lesions | | Cartilage erosions | No gross lesions | Lesion (erosion) | Cartilage lesions | No gross lesions |

TABLE 10

Clinical assessment (+21 d IA)

| 21 d IA | 1584 BII |
|---|---|
| Lameness | 0/5 |
| Joint swelling | 1/3 |
| Joint pain on flexion | 0/3 |
| Other | |

TABLE 11

(+28 d IA)

| 28 d IA | 1584 BII |
|---|---|
| Lameness | 1/5 |
| Joint swelling | 1/3 |
| Joint pain on flexion | 0/3 |
| Necropsy Results synovium | thickening+ |
| Articular cartilage | No gross lesions |

Figure 4:
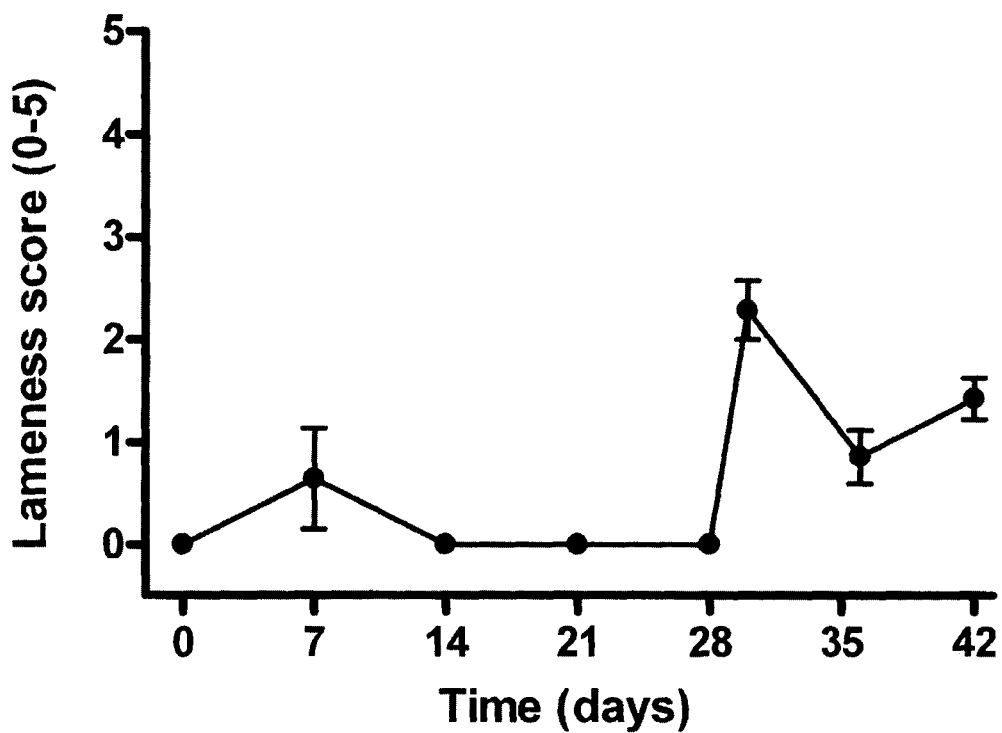
FIG. 4 is a graphical representation showing lameness score of a sheep model of rheumatoid arthritis. Scores were determined as described herein.

FIG. 4 shows the mean lameness score for sheep following intrarticular collagen type II injection. As shown lameness increased at about 28 days after the first collagen type II injection.

Figure 5:
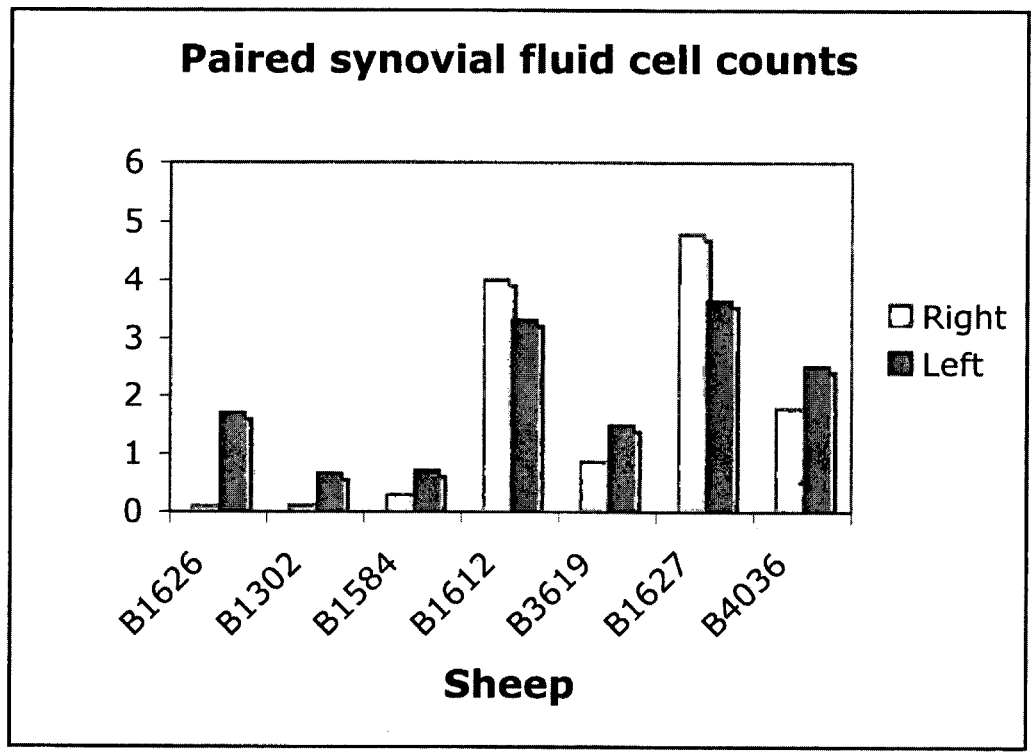
FIG. 5 is a graphical representation showing leukocyte counts in the synovial fluid from right (unstimulated) and left (stimulated) hocks of individual sheep during the course of the trial (as indicated in the drawing). Sheep B1627 and B4036 were immunised with chicken Type II collagen and all other sheep were immunised with bovine Type II collagen. In the higher responders the leukocyte concentration in the control side was also raised indicating the possibility of a systemic response.
Figure 6:
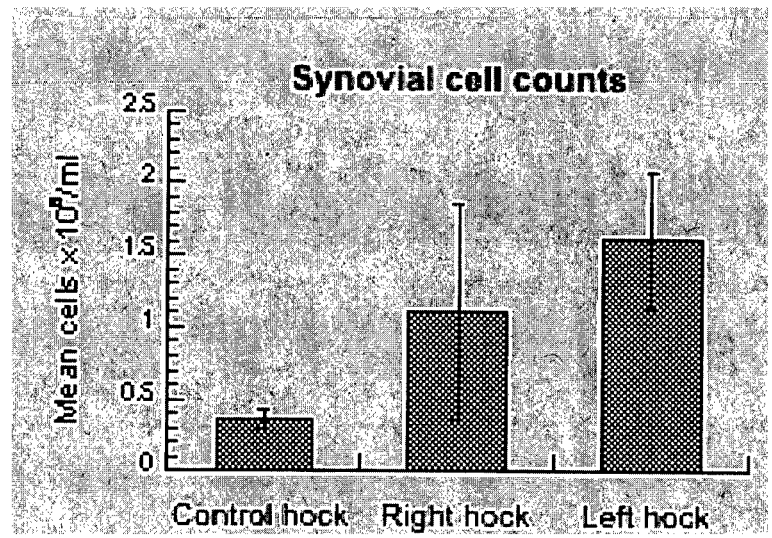
FIG. 6 is a graphical representation showing leukocyte counts in the synovial fluid of control sheep (n=7) and sheep immunised with bovine Type II collagen (n=5). Data shows the mean±standard error.

FIG. 5 shows leukocyte counts in synovial fluid from right (unstimulated) and let (stimulated) hocks of individual sheep. In the higher responders the leukocyte concentration in the control side was also raised indicating the possibility of a systemic response. FIG. 6 shows mean leukocyte counts in the synovial fluid of control sheep and sheep immunized with bovine type II collagen.

Figure 7A:
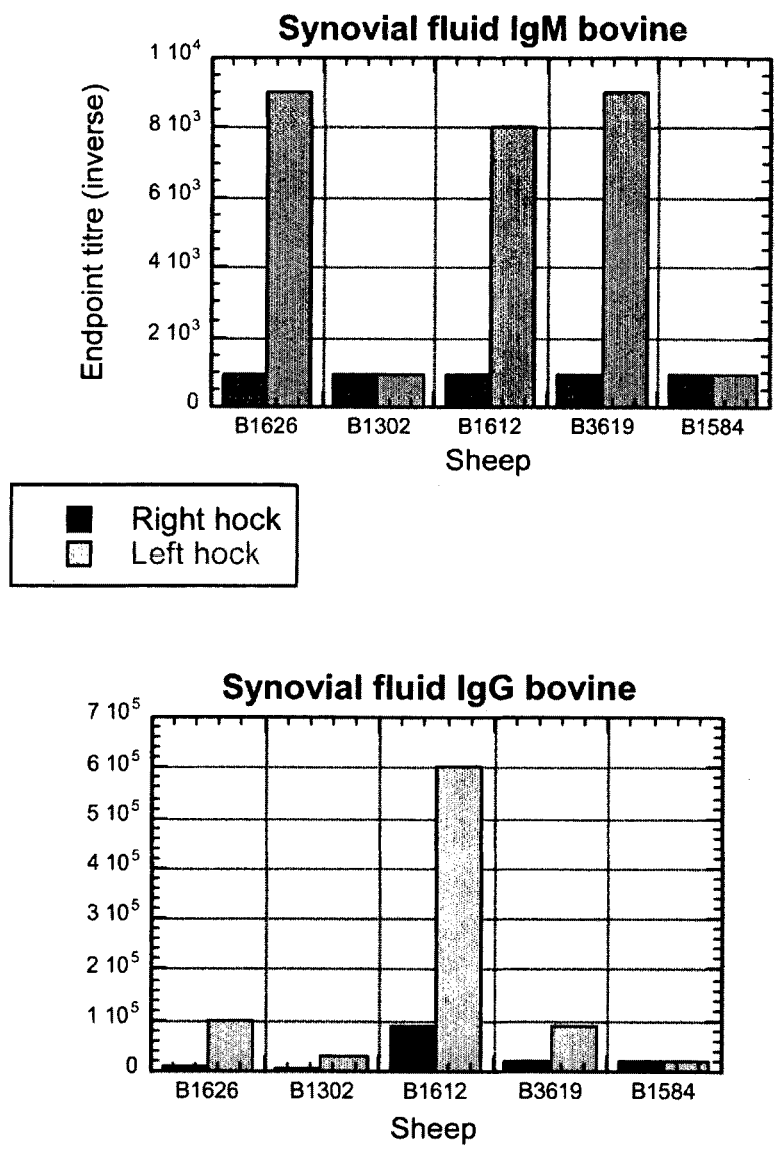
FIG. 7A is a graphical representation showing levels of IgM (left hand panel) and IgG (right hand panel) antibodies to bovine Type II collagen in the synovial fluid from right (control) and left (stimulated) hocks of 5 sheep immunised with bovine Type II collagen. Synovial fluid was taken at autopsy, 42 days after initial immunisation. Levels of IgM were raised 4-8 fold and levels of IgG were raised 10-60 fold in the stimulated hocks.
Figure 7B:
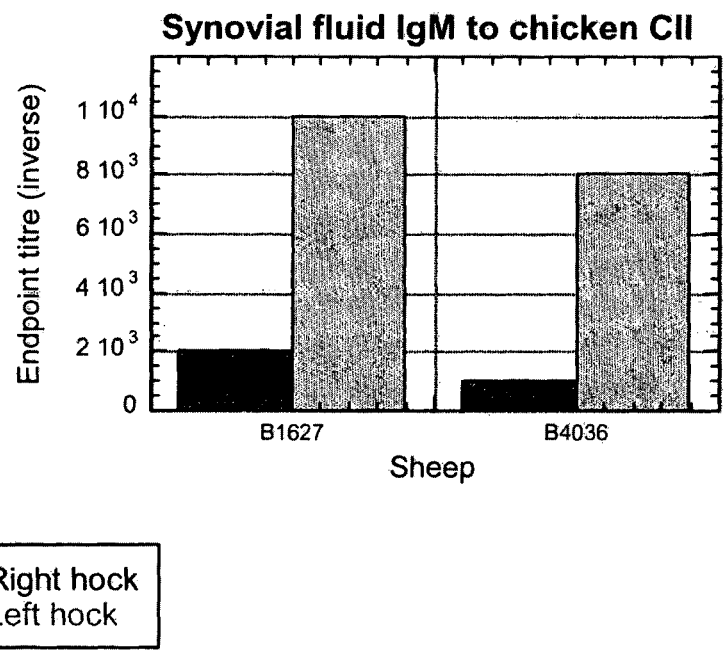
FIG. 7B is a graphical representation showing levels of IgM (left hand panel) and IgG (right hand panel) antibodies to chicken Type II collagen in the synovial fluid from right (control) and left (stimulated) hocks of 2 sheep immunised with chicken Type II collagen. Synovial fluid was taken at autopsy, 42 days after initial immunisation. Levels of IgM were raised 3-5 fold and levels of IgG were raised 2–8×10⁶ fold in the stimulated hocks.
Figure 7B:
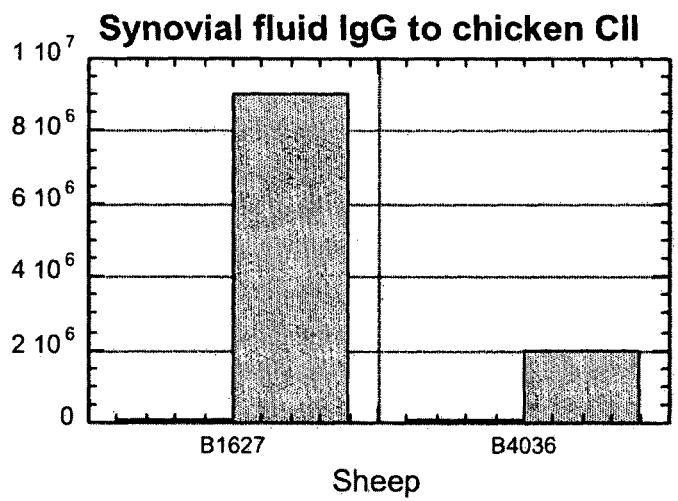

FIGS. 7A and 7B show levels of IgM and IgG antibodies in synovial fluid from sheep immunized with bovine type II collagen and chicken type II collagen, respectively. These results indicate increased IgM and IgG against type II collagen in immunized hocks of these animals. These data are also summarized in Table 12.

TABLE 12

Relative levels of antibodies to bovine or chicken Type II collagen in the plasma of immunised sheep

| Sheep | Synovitis score* Left hock/Right hock | Plasma IgM: day 14 Endpoint titre** | Plasma IgG: day 28 Endpoint titre |
|---|---|---|---|
| Bovine | | | |
| B1626 | 5/4 | $9 \times 10^3$ | $9 \times 10^4$ |
| B1302 | 4/3 | $9 \times 10^3$ | $9 \times 10^4$ |
| B1584 | 3/2.5 | $1 \times 10^4$ | $9 \times 10^4$ |
| B1612 | 9/5 | $1 \times 10^4$ | $9 \times 10^6$ |
| 83619 | 9/4 | $1 \times 10^4$ | $9 \times 10^6$ |

TABLE 12-continued

Relative levels of antibodies to bovine or chicken Type II collagen in the plasma of immunised sheep

| Sheep | Synovitis score* Left hock/Right hock | Plasma IgM: day 14 Endpoint titre** | Plasma IgG: day 28 Endpoint titre |
|---|---|---|---|
| Chicken | | | |
| B1627 | 6/3 | $9 \times 10^4$ | $1 \times 10^7$ |
| B4036 | 6/3 | $9 \times 10^4$ | $1 \times 10^7$ |

*The grading system incorporates three morphological criteria: hyperplasia of the synovial cell layer, inflammatory infiltration and activation of the synovial stroma and has a maximum score of 9 (Krenn et al, Pathol Res. Pract. 198: 317-325, 2002).
**IgM levels were highest at day 14.

The data presented above show that collagen induced arthritis (CIA) was induced in 7 sheep by the subcutaneous injection of heterologous type II collagen in Freund's adjuvant on day 0 and day 14 and the intra-articular injection of type II collagen into the hock joint on day 28. The disease progressed rapidly and by 14 days after the intra-articular injection of CII was characterized by joint inflammation, synovial hyperplasia, mononuclear cell infiltration, anti collagen type II antibodies and in some sheep erosive lesions of the articular cartilage. Clinical signs of lameness were evident in all 7 sheep and gross thickening of the synovium surrounding the tibiotarsal joint was evident in 6 of the 7 sheep.

CIA in sheep appears to be an excellent large animal model of arthritis with significant similarities to human rheumatoid arthritis.

Example 5

Experimental Design

A sheep model of rheumatoid arthritis is produced essentially as described in Example 4.

Thirty-six sheep will be randomly allocated to one of six (6) groups, each including eight (6) sheep, as shown in Table 13. Test articles will be administered to relevant animals 42 days post the first collagen injection.

Thirty days after the administration of the test articles, the sheep will be euthanised and gross necropsy examination conducted and tissue collected for pathology and histological examination.

TABLE 13

Treatment Assignment

| Group ID | No. of animals | Type | MPC Dose | Route | Timing | Sacrifice |
|---|---|---|---|---|---|---|
| A | 6 | oMPCs | 0.3 Million/kg | IV | Day 42 | Day 72 |
| B | 6 | oMPCs | 1.0 Million/kg | IV | Day 42 | Day 72 |
| C | 6 | oMPCs | 2.0 Million/kg | IV | Day 42 | Day 72 |
| D | 6 | Control (saline) | N/A | IV | Day 42 | Day 72 |
| E | 6 | oMPCs | 25 Million | Intra-articular | Day 42 | Day 72 |
| F | 6 | Control (saline) | N/A | Intra-articular | Day 42 | Day 72 |

Preparation of MPC doses 24 million ovine MPCs (oMPCs) in 4.0 mL ProFreeze®/DMSO/Alpha-MEM (to be used to provide a dose of 0.3 million oMPCs/kg by IV injection)

80 million oMPCs in 4.0 mL ProFreeze®/DMSO/Alpha-MEM (to be used to provide a dose of 1 million oMPCs/kg by IV injection)

160 million oMPCs in 4.0 mL ProFreeze®/DMSO/Alpha-MEM (to be used to provide a dose of 2 million oMPCs/kg by IV injection)

35 million oMPCs in 0.7 mL ProFreeze®/DMSO/Alpha-MEM (to be used to provide a dose of 25 million oMPCs by intra-articular injection)

Sterile saline (control).

Gross Pathology

Necropsy and tissue collection is performed on all animals that die or are euthanised. Collected tissues is fixed in 10% buffered formalin. Macroscopic findings are recorded for each tissue.

The left (treated) and right (control) hock joints are exposed and dissected down to the synovial membrane. Samples of synovium (and underlying fat) is placed in either 10% buffered neutral formalin for fixing or OCT compound for snap freezing.

The joints are then disarticulated and the articular surfaces examined for evidence of gross cartilage lesions and photographed. Segments of the articular surface of the talus bone (see below) are removed using a saw, and fixed in 10% buffered neutral formalin.

Histopathological Scoring of Synovial Tissues from Hock joints

The methodology for the preparation of histological sections and scoring of pathological changes within the synovial membrane and subsynovial tissues of the left and right hock joint of control and treated animals was based on the publication of Krenn et al (Pathol Res. Pract. 198:317-325).

Immunohistochemical Studies and Scoring of Synovial Tissues from Hock Joints

Synovial membrane was collected from the dorso-lateral and dorso-medial region of the right and left tibiotarsal (Hock) joints from treated and control animals. These tissues were frozen in OCT compound and sectioned using a cryostat onto glass slides. Sections were subjected to staining using standard immunohistochemical methods for the identification of specific cell types and antibodies following published methodologies (16) and commercially available protocols. The antibodies used included those raised against CD4 (44-97), CD8 (38-65), gamma-delta (γδ T cells (86D/127-5), CD14 (VMRD a-M-M9), B cell (CD79a: HM57) and the cytokines TNF-alpha, Interleukin-6, interleukin-1beta, interleukin-17, Interleukin-10, Interferon gamma, Factor VIII and VCAM-1 and were obtained from commercial sources or prepared in house. The stained sections were scored blinded.

Clinical Pathology

Approximately 30-40 mL of blood was collected at pre-study entry, Day 0 (Baseline), Day 42, Day 49, Day 56, Day 63 and at necropsy (Day 72) and used for the following assays:

Cytokines: The levels of the cytokines, TNF-a, IFN-g, IL-1b and IL-6, in synovial fluid and plasma were determined.

Statistical Methods

Statistical analysis and graphical representation of the data obtained for the various treatment groups was undertaken using one way ANOVA followed by Tukey's or Newman-Keuls multiple comparison tests using Graphpad Prism Statistical software (version 5.0b) (GraphPad Software Inc, La Jolla, Calif. USA). Statistical significance between treatment groups was taken as $p<0.05$. For parametric data significance between individual treatment groups and controls was determined using the paired Student's t-test. For non-parametric assessment, differences between groups were evaluated using the Mann-Whitney or the Wilcoxon matched-pairs signed rank tests with significance accepted at $p<0.05$.

Example 6

Results of Histopathological Scoring of Synovial Tissues from Hock Joints

Figure 8A:
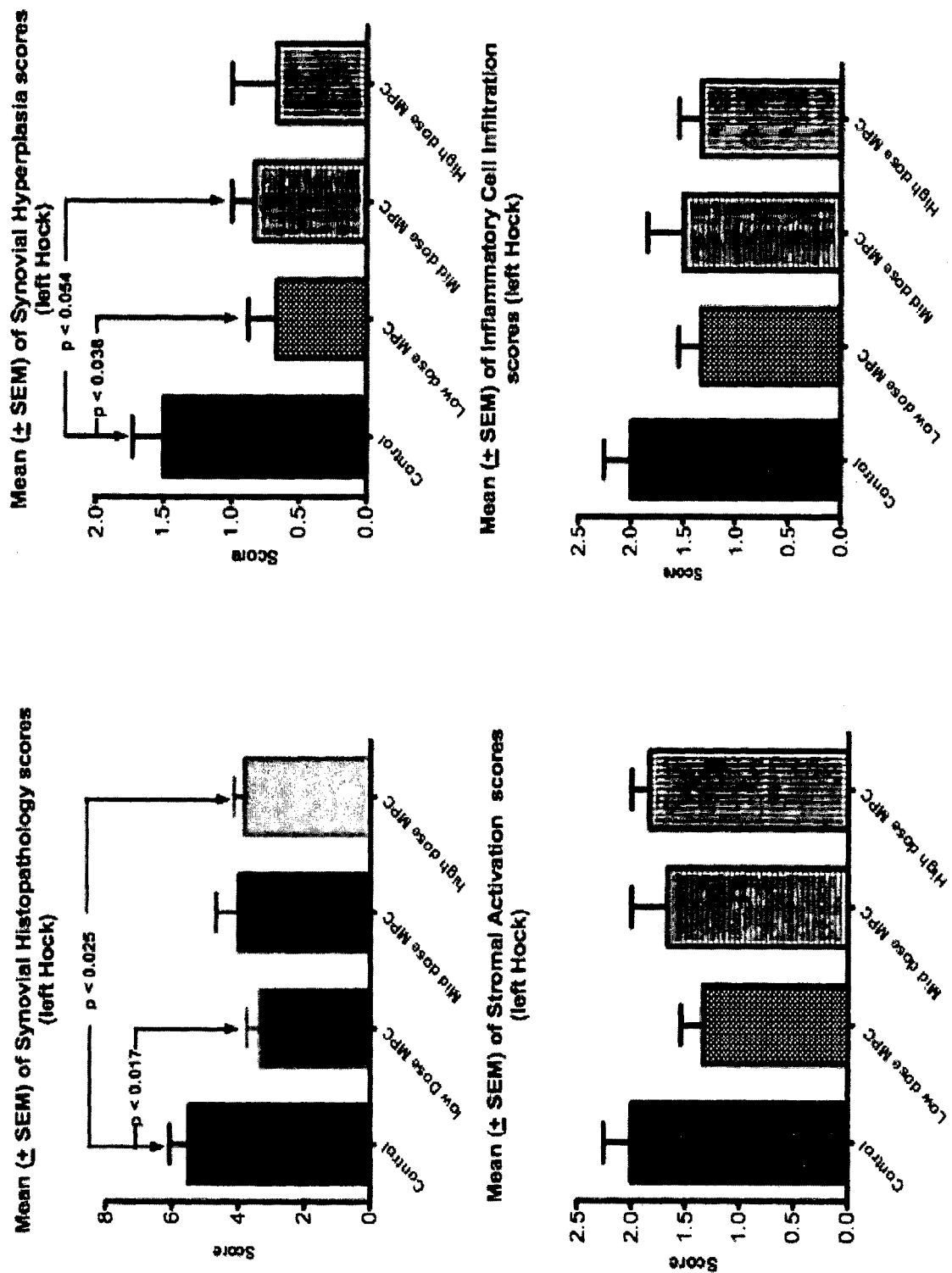
FIG. 8A shows aggregate and individual histopathology scores (hyperplasia, stromal activation, inflammatory cell infiltrate) for synovial membranes from left hock joints of all groups. Anova=p<0.04; p from Mann-Whitney test.
Figure 8B:
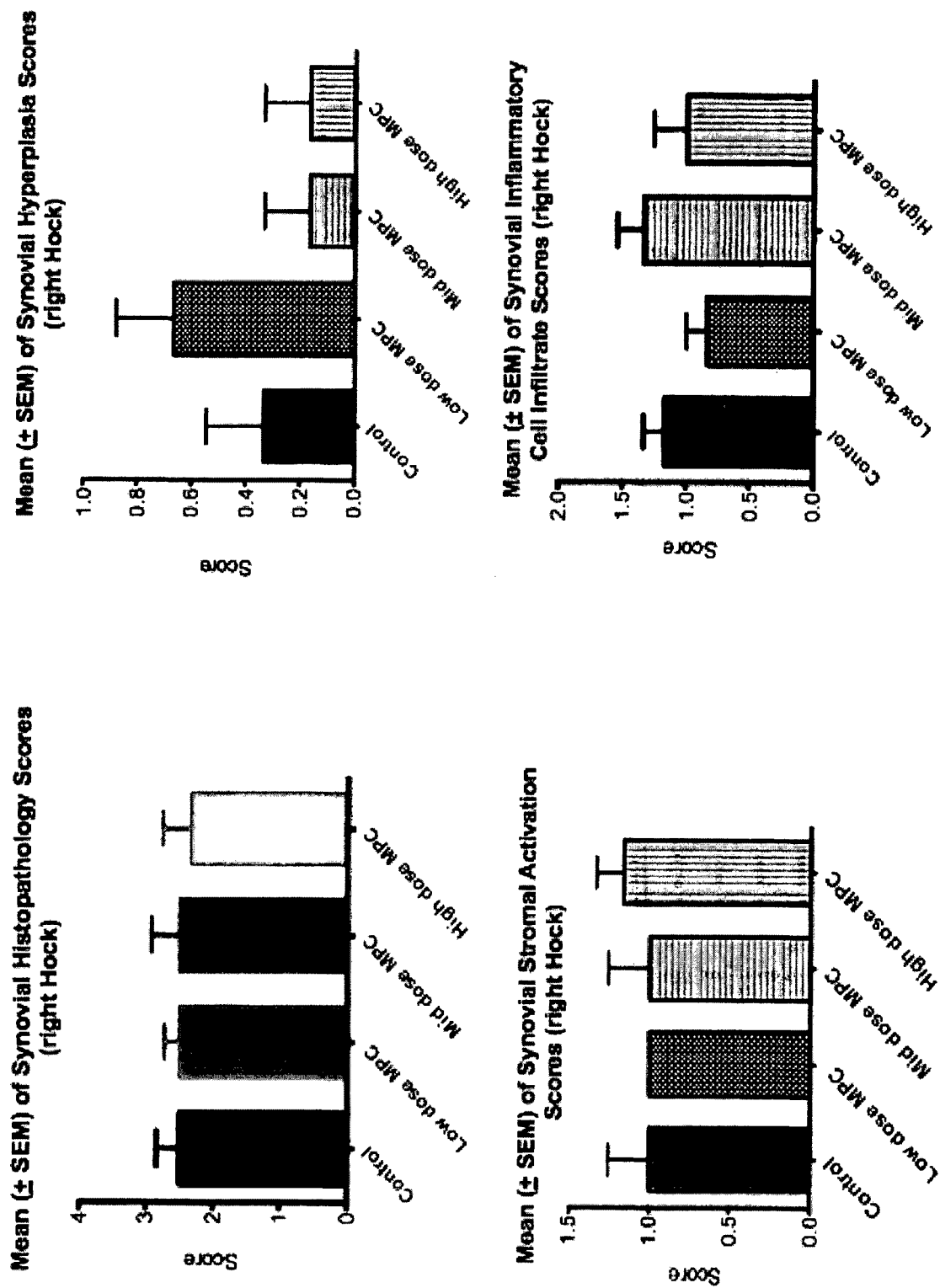
FIG. 8B shows aggregate and individual histopathology for synovial membranes from right hock joints of all IV injected groups.

The individual histopathological scores for the synovial membranes of left (bovine type II collagen (BII) injected joint) and right Hock joints of all animals were determined by blinded observers. The aggregate and component score for each section obtained by summation of the individual scores for hyperplasia, stromal (synovial tissue) activation, and inflammatory infiltrate are summarised graphically in FIGS. 8A and 8B. From these figures it is evident that the aggregate score for the BII injected left joints was higher than for the scores for the contralateral right joints. Moreover, statistically significant differences between the MPC treated groups and the control group were demonstrated for the low ($p<0.017$) and high ($p<0.025$) MPC injected groups (FIG. 8A) but not for any of the group histopathological scores for the corresponding synovium in the right joints (FIG. 8B). The major contribution to the differences between control and MPC treated groups would appear to be in the reduction in synovial hyperplasia in the cell treated groups (FIG. 8A).

Figure 8C:
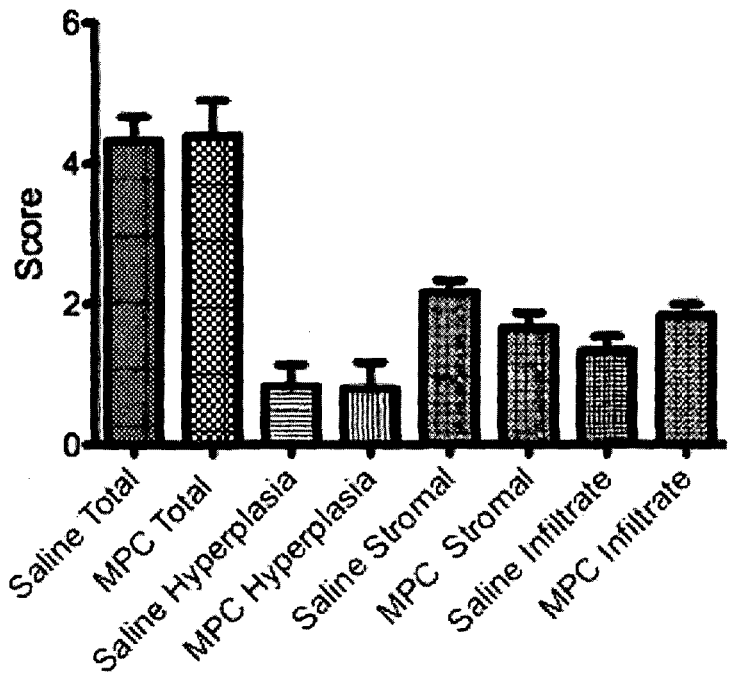
FIG. 8C shows aggregate and individual histopathology scores for synovial membranes from groups injected Intra-articularly (IA) with saline or MPC.
Figure 8C:
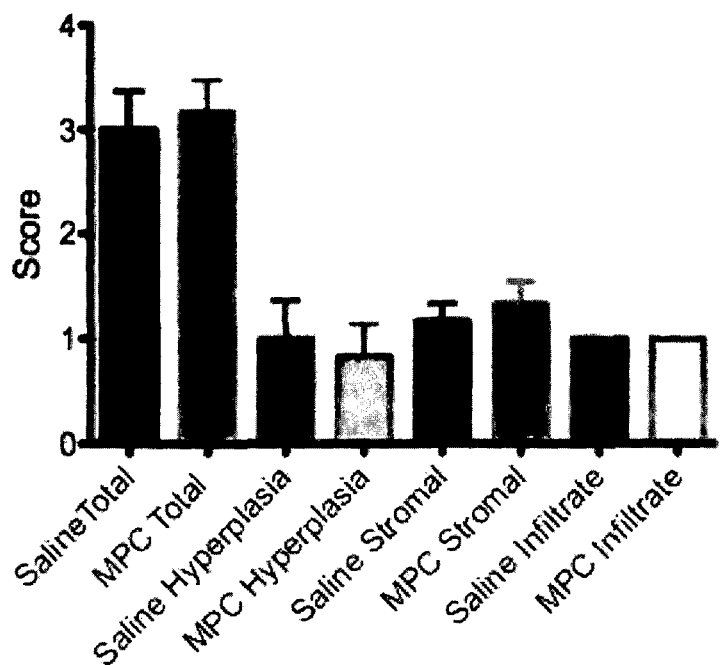

The scores of synovial histopathological changes in the left and right hock joints of the intra-articular injected groups failed to show any significant differences between injection with saline or 25 million MPC but as expected the scores for the left joints were higher than the right joint (FIG. 8C).

Example 7

Immunohistochemical Studies of the Synovial Tissues

The results of the scoring systems used to semi-quantify the cellular changes and cytokine levels in the synovial tissues of the various animal groups following immunohistolochemical staining with the antibodies described in the methods section are shown in FIGS. 9A-9C. The use of 3 different methods of scoring these multiple sections precluded the generation of a meaningful combined score for each of the experimental groups examined. Therefore the mean scores obtained for each of the experimental groups for the individual marker antibodies used are presented separately and are shown in FIGS. 10A-10F. Representative photomicrograph examples of some these sections together with the scores assigned are shown in FIGS. 11A-11E.

Figure 10A:
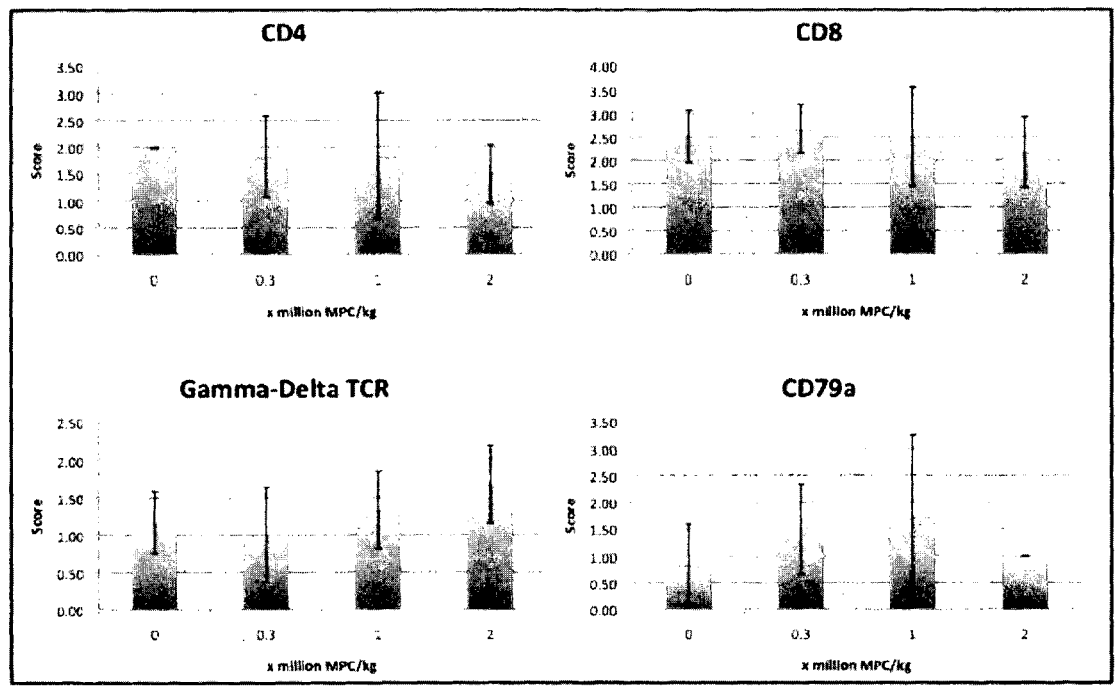
FIG. 10A shows mean±SD immunohistological scores for CD4, CD8, Gamma-delta TCR and CD79a in left hock joint synovial tissues for the control and MPC injected groups.
Figure 10B:
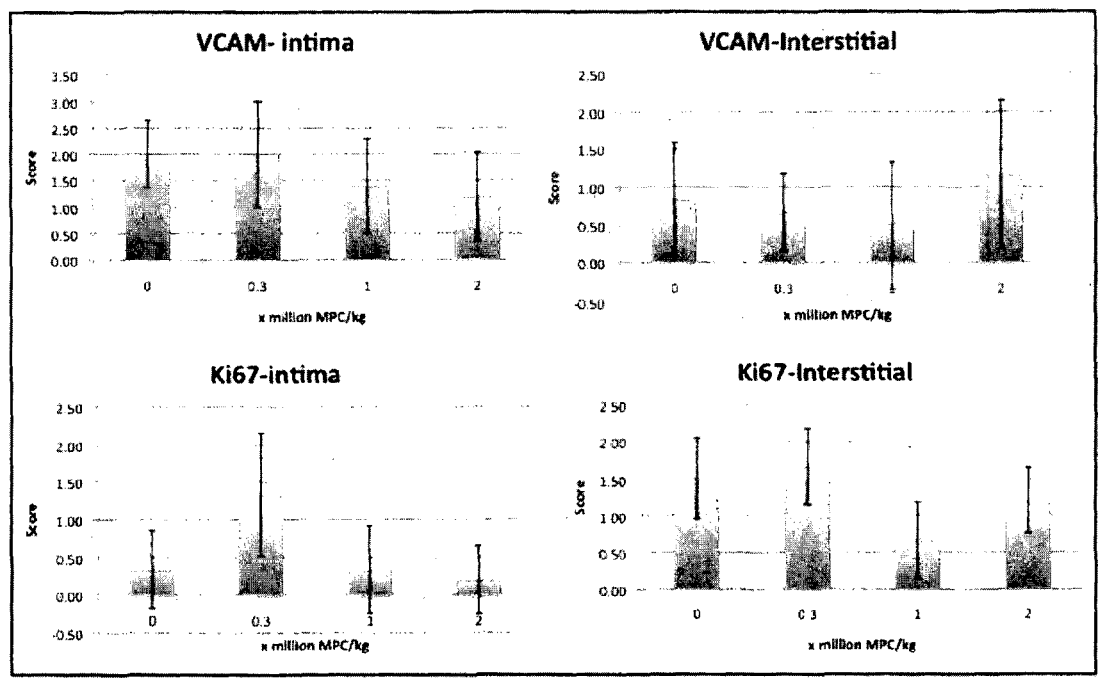
FIG. 10B shows mean±SD immunohistological scores for VCAM-intima, VCAM-interstitial, Ki67-intima and Ki67-interstitial in left hock joint synovial tissues for the control and MPC injected groups.
Figure 10C:
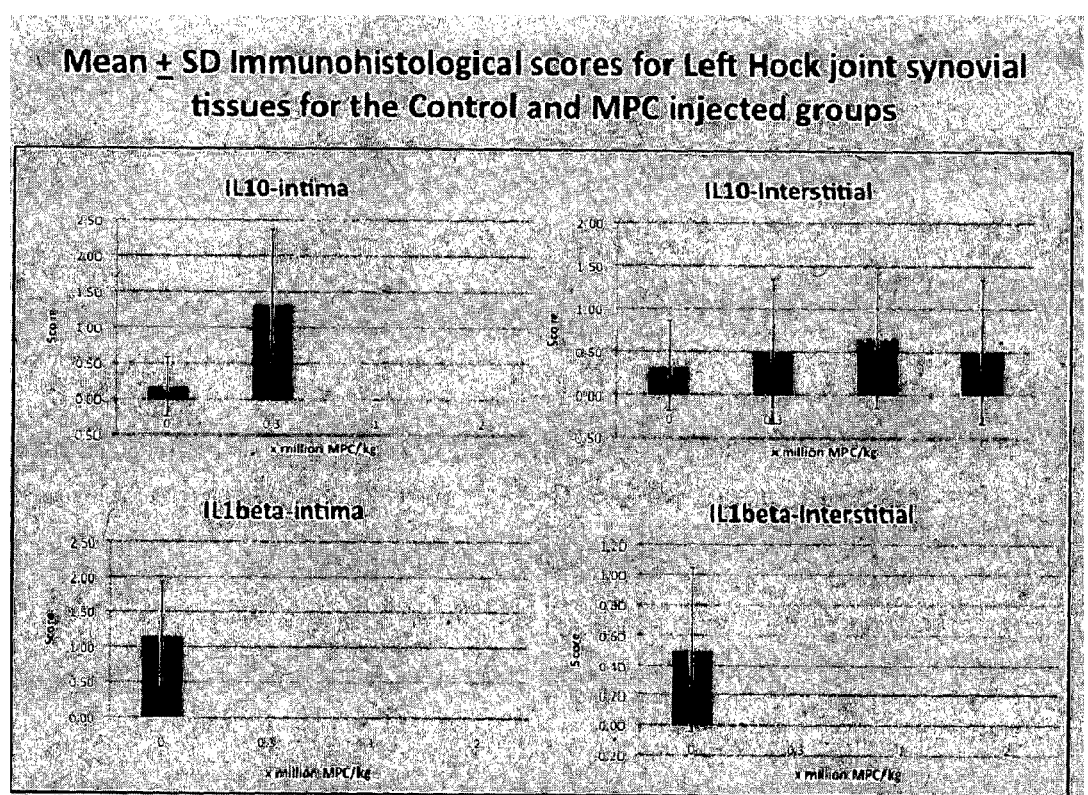
FIG. 10C shows mean±SD immunohistological scores for IL-10-intima, IL-10-interstitial, IL1beta-intima and IL1beta-interstitial in left hock joint synovial tissues for the control and MPC injected groups.
Figure 10D:
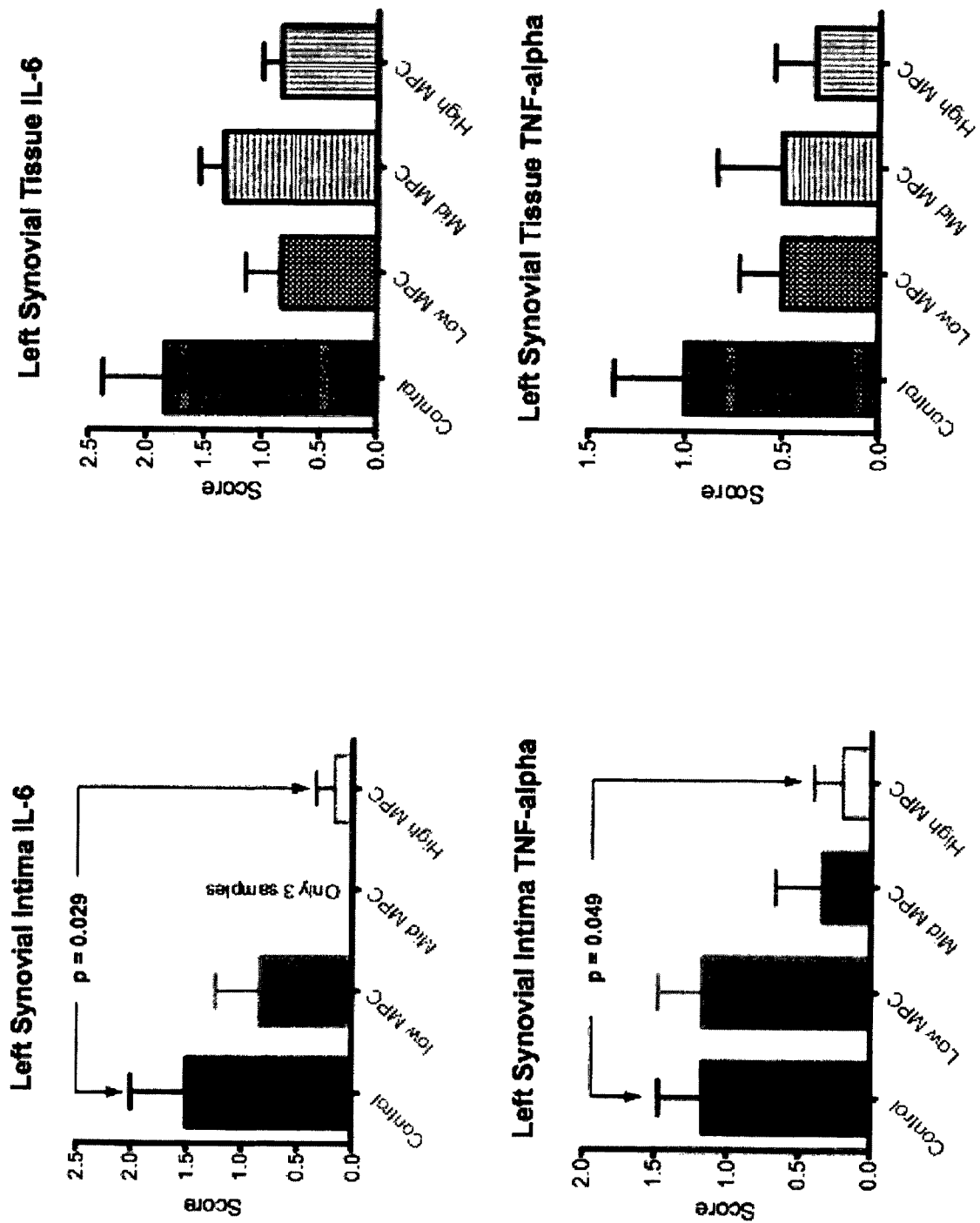
FIG. 10D shows mean±SEM for synovial immunohistochemical staining scores for IL-6 and TNF-alpha for the synovial intima and interstitial tissues of the IV saline control and MPC injected groups. The p values shown were calculated using the Mann-Whitney non-parametric t-test.
Figure 10E:
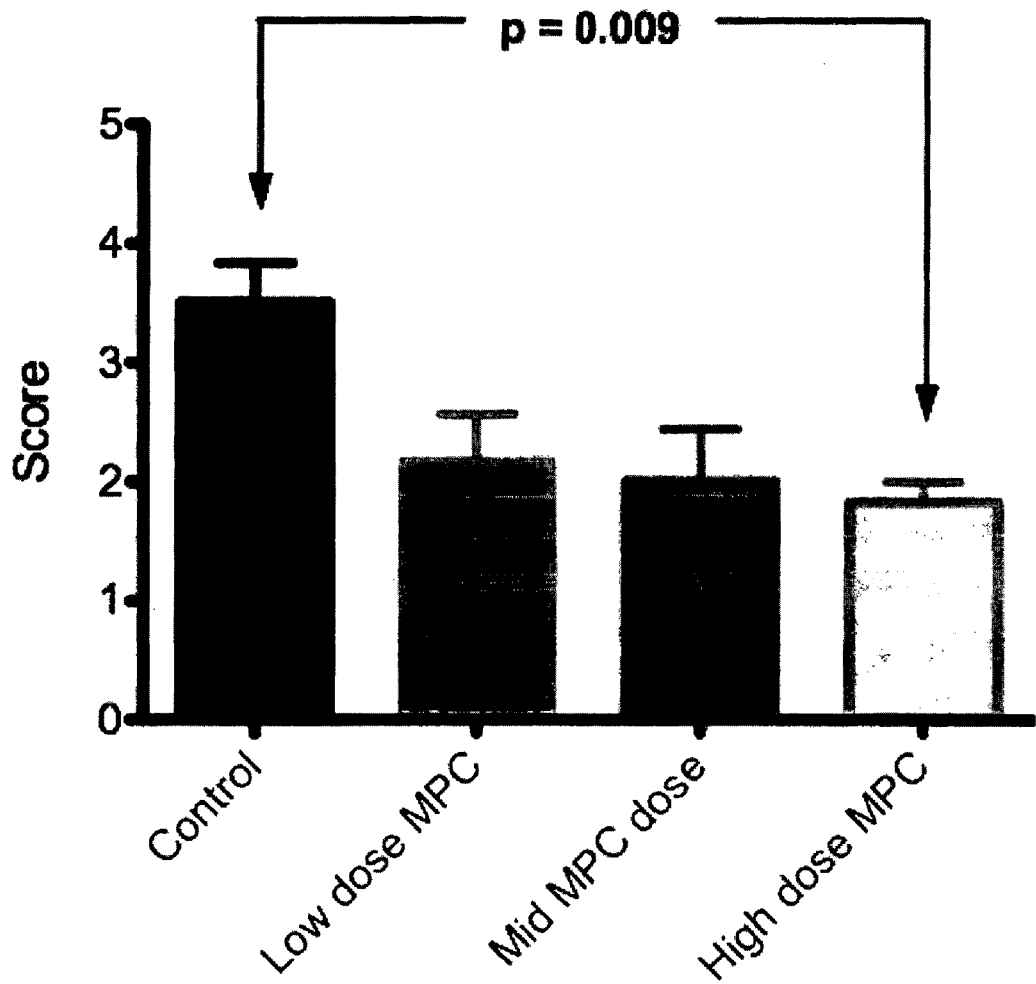
FIG. 10E shows mean±SEM for synovial immunohistochemical interstitial tissue staining for CD14 positive cells for saline control and MPC injected groups. The p values shown were calculated using the Mann-Whitney non-parametric t-test.
Figure 10F:
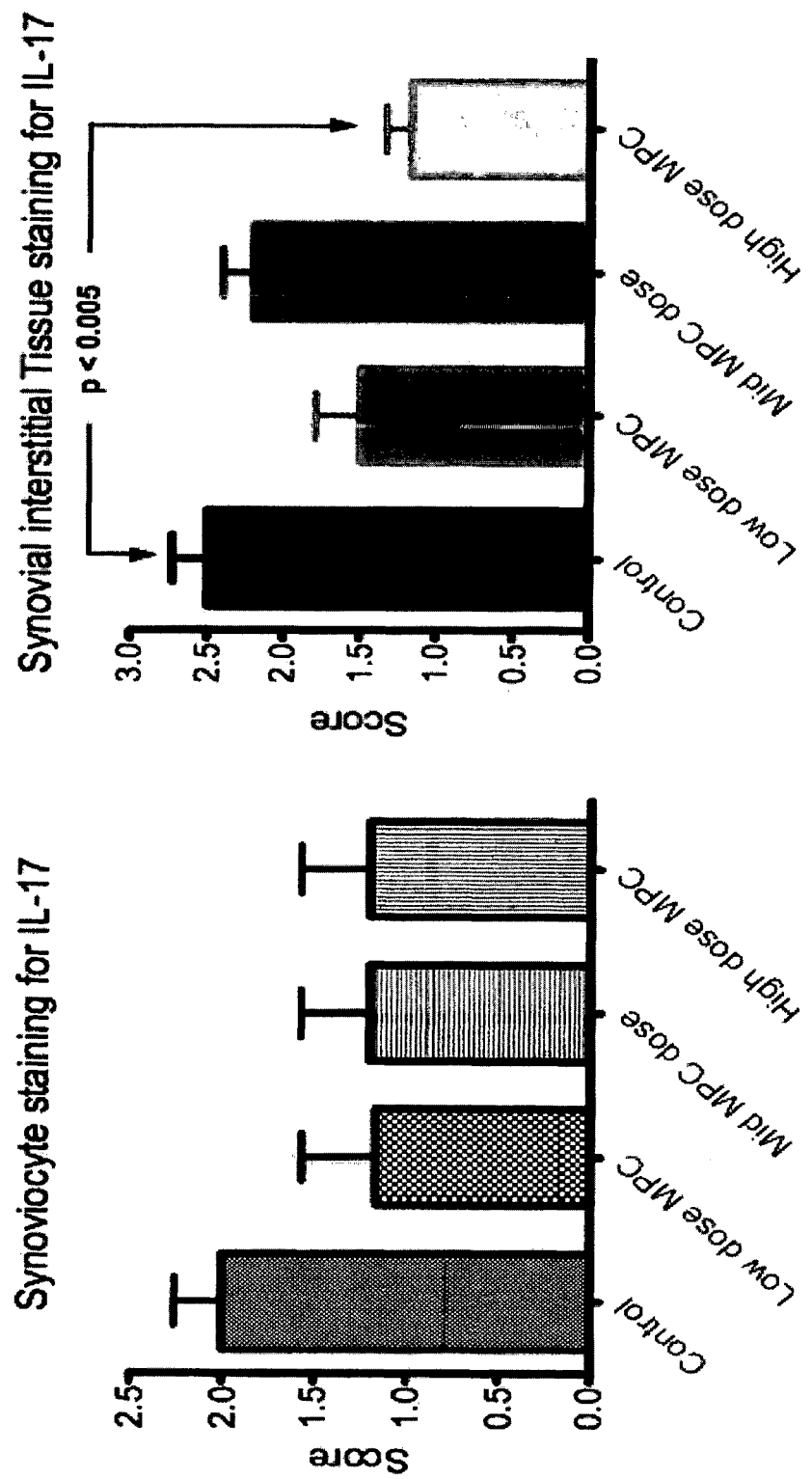
FIG. 10F shows mean±SEM for synovial immunohistochemical interstitial tissue staining for IL-17 for saline control and MPC injected groups. The p values shown were derived from ANOVA with Krushal-Wallis test & Dunns post-hoc test.
Figure 11A:
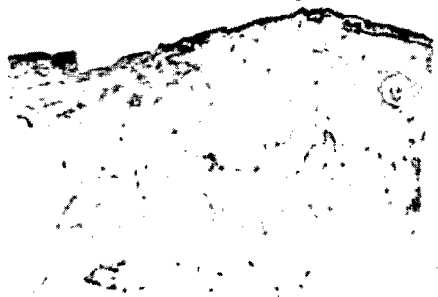
FIG. 11A shows photomicrographs of synovial sections immunostained for CD14 cells showing assigned scores. Magnification×100.
Figure 11A:
Figure 11A:
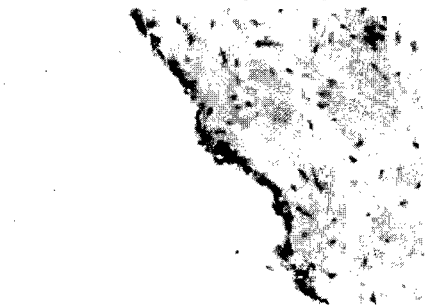
Figure 11A:
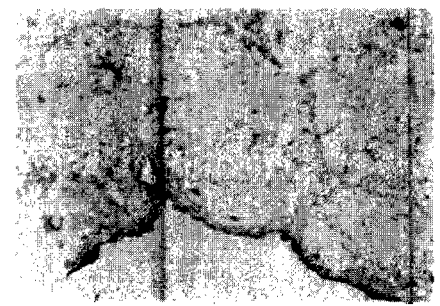
Figure 11B:
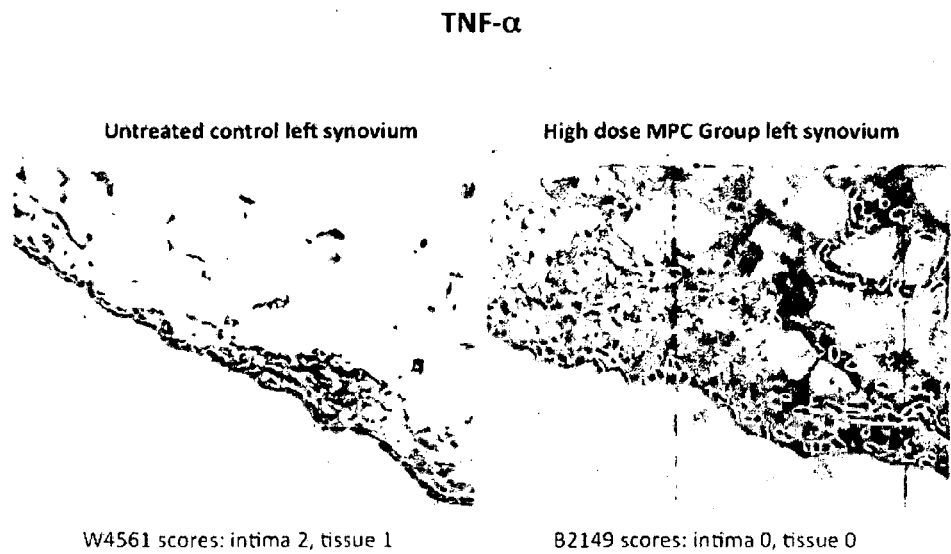
FIG. 11B shows photomicrographs of synovial sections immunostained for TNF-α showing assigned scores. Magnification×100.
Figure 11C:
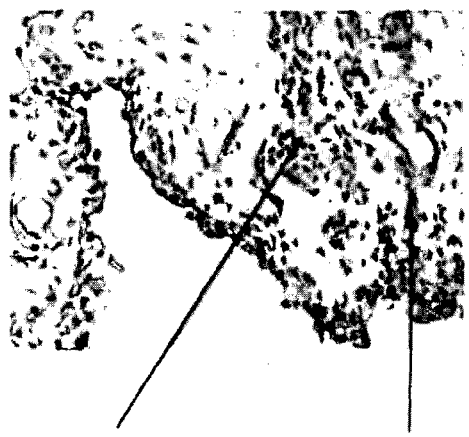
FIG. 11C shows photomicrographs of synovial sections showing immunostained for IL-6 showing assigned scores. Magnification×100.
Figure 11C:
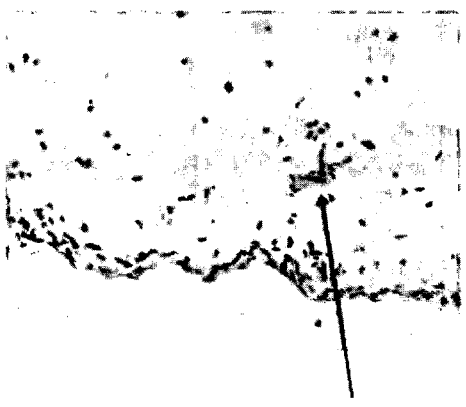
Figure 11D:
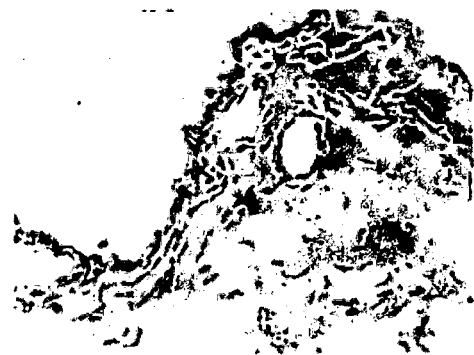
FIG. 11D shows photomicrographs of synovial sections immunostained for IL-17 showing assigned scores. Magnification×100.
Figure 11D:
Figure 11E:
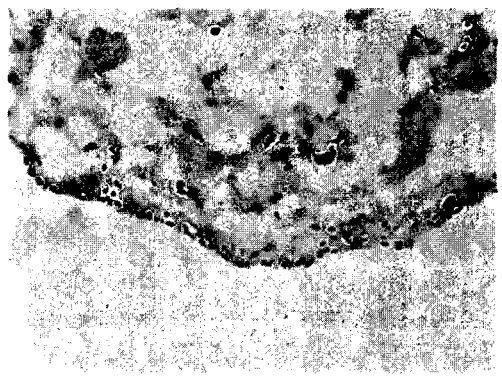
FIG. 11E shows photomicrographs of synovial sections immunostained for IL-10 showing assigned scores. Magnification×100.
Figure 11E:
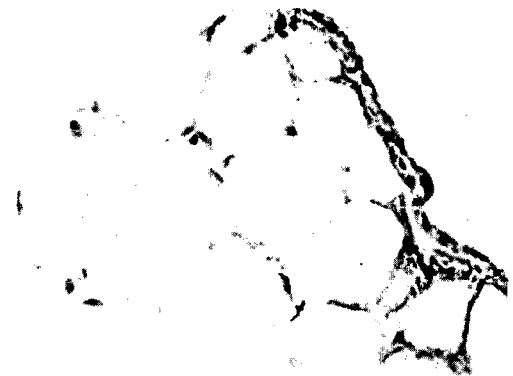

Although clear trends were apparent for a decrease in intimal IL-1 and VCAM-1 and an increase in Gamma-Delta TCR (FIGS. 10A-10C) no statistically significant differences between the Control and MPC injected groups could be demonstrated. However, synovial intima (synoviocyte) staining for IL-6 ($p=0.029$) and TNF-alpha ($p=0.049$) (FIG. 10D) and interstitial tissues staining for CD-14 cells (FIG. 10E) for the high MPC dose injected group was demonstrated to be significantly lower than the saline injected control group ($p=0.009$). Furthermore, levels of the cytokine IL-17 in the synovial interstitial tissues of the high dose group were also significantly lower than for the corresponding control group (ANOVA, $p<0.005$) (FIG. 10F).

The results of the immunohistochemical scores obtained for the saline and MPC injected joints are shown in Table 14. There appeared to be higher staining for CD4, CD8 and CD79 in the MPC injected joints a finding which was consistent with the higher number of lymphocytes observed in the MPC injected joints. However, the mean values for TNF-alpha and IL-17 in the MPC injected joints were lower than for the saline injected joints, particularly for the intima region of the left joint synovium.

TABLE 14

Immunohistochemical scores for synovial tissues of hock joints from RA animals injected intra-articularly with Saline or 25 million MPC. L = Left joint, R = Right joint, LI = Left joint intima, RI = Right intima. LT = Left interstitial Tissue, RT = Right interstitial Tissue

| Group | | CD4 | | CD8 | | γδ TCR | | CD79a | | CD14 | | | |
|---|---|---|---|---|---|---|---|---|---|---|---|---|---|
| | | | | | | | | | | Left | Left | Right | Right |
| Joint Tissue | Sheep | Left | Right | Left | Right | Left | Right | Left | Right | intima | tissue | intima | tissue |
| F(Saline) | Y28 | 3 | 0 | 3 | 2 | 2 | 0 | 1 | 0 | 3 | 3 | 2 | 1 |
| IA | Y31 | 1 | 2 | 2 | 2 | 2 | 1 | 2 | 1 | no intima | 2 | no intima | 1 |
| | Y30 | 1 | 1 | 1 | 2 | 1 | 0 | 1 | 1 | 3 | 1 | 2 | 1 |
| | Y34 | 2 | 1 | 1 | 1 | 1 | 1 | 1 | 0 | no intima | 3 | no intima | 2 |
| | Y37 | 1 | 1 | 2 | 1 | 1 | 1 | 2 | 0 | 3 | 4 | 3 | 2 |
| | Y39 | 2 | 1 | 2 | 1 | 1 | 1 | 2 | 1 | 2 | 3 | 1 | 2 |
| mean | | 1.67 | 1.00 | 1.83 | 1.50 | 1.33 | 0.67 | 1.50 | 0.50 | 2.75 | 2.67 | 2.00 | 1.50 |
| SD | | 0.82 | 0.63 | 0.75 | 0.55 | 0.52 | 0.52 | 0.55 | 0.55 | 0.50 | 1.03 | 0.82 | 0.55 |
| E(MPC) | Y26 | 4 | 0 | 4 | 0 | 2 | 0 | 2 | 0 | 2 | 2 | 2 | 1 |
| IA | Y27 | 1 | 0 | 2 | 1 | 1 | 1 | 1 | 0 | 2 | 3 | 3 | 1 |
| | Y29 | 4 | 1 | 4 | 1 | 2 | 2 | 2 | 1 | 2 | 3 | 2 | 1 |
| | Y32 | 2 | 1 | 1 | 1 | 0 | 1 | 3 | 0 | 2 | 2 | 2 | 2 |
| | Y38 | 2 | 1 | 3 | 2 | 2 | 1 | 2 | 2 | 2 | 2 | 4 | 2 |
| | Y40 | 4 | 2 | 4 | 1 | 2 | 1 | 3 | 0 | 3 | 3 | 2 | 1 |
| mean | | 2.83 | 0.83 | 3.00 | 1.00 | 1.50 | 1.00 | 2.17 | 0.50 | 2.17 | 2.50 | 2.50 | 1.33 |
| SD | | 1.33 | 0.75 | 1.26 | 0.63 | 0.84 | 0.63 | 0.75 | 0.84 | 0.41 | 0.55 | 0.84 | 0.52 |

TABLE 14-continued

Immunohistochemical scores for synovial tissues of hock joints from RA animals injected intra-articularly with Saline or 25 million MPC. L = Left joint, R = Right joint, LI = Left joint intima, RI = Right intima. LT = Left interstitial Tissue, RT = Right interstitial Tissue

| Group | | VCAM-1 | | | | IL-6 | | | | Ki67 | | | | Factor VIII | |
|---|---|---|---|---|---|---|---|---|---|---|---|---|---|---|---|
| Joint | | Left | Left | Right | Right | Left | Left | Right | Right | Left | Left | Right | Right | | |
| Tissue | Sheep | intima | tissue | intima | tissue | intima | tissue | intima | tissue | intima | tissue | intima | tissue | Left | Right |
| F (Saline) IA | Y28 | 0 | 1 | 1 | 0 | no intima | 0 | 0 | 0 | no intima | 3 | 0 | 0 | 23 | 27 |
| | Y31 | 3 | 2 | 1 | 0 | 2 | 3 | 0 | 2 | 0 | 2 | 0 | 1 | 79 | 14 |
| | Y30 | 2 | 1 | 2 | 0 | 1 | 2 | 0 | 1 | 0 | 0 | 0 | 0 | 34 | 20 |
| | Y34 | no Intima | 1 | no intima | 0 | no Intima | 4 | no intima | 1 | no intima | no intima | | 0 | 45 | 17 |
| | Y37 | 2 | 1 | 1 | 1 | 0 | 1 | 0 | 0 | 0 | 1 | 0 | 0 | 59 | 36 |
| | Y39 | 1 | 1 | 1 | 0 | 1 | 3 | 0 | 1 | 0 | 0 | no intima | 0 | 44 | 57 |
| mean | | 1.60 | 1.17 | 1.20 | 0.17 | 1.00 | 2.17 | 0.00 | 0.83 | 0.00 | 1.20 | 0.00 | 0.17 | 47.03 | 28.39 |
| SD | | 1.14 | 0.41 | 0.45 | 0.41 | 0.82 | 1.47 | 0.00 | 0.75 | 0.00 | 1.30 | 0.00 | 0.41 | 19.59 | 15.76 |
| E(MPC) IA | Y26 | 0 | 1 | 0 | 0 | 2 | 2 | 0 | 1 | 0 | 2 | 0 | 0 | 47 | 18 |
| | Y27 | 2 | 1 | 2 | 0 | 1 | 1 | 0 | 1 | 0 | 1 | 0 | 0 | 80 | 22 |
| | Y29 | 2 | 1 | 2 | 0 | 1 | 3 | 0 | 3 | | 2 | | 0 | 39 | 32 |
| | Y32 | 1 | 0 | 1 | 1 | 0 | 3 | 0 | 2 | 0 | 0 | 0 | 0 | 29 | 28 |
| | Y38 | 2 | 0 | 1 | 0 | 0 | 2 | 0 | 1 | 0 | 1 | 0 | 0 | 36 | 32 |
| | Y40 | 3 | 2 | 2 | 1 | 1 | 2 | | | 1 | 1 | 0 | | 45 | 40 |
| mean | | 1.67 | 0.83 | 1.33 | 0.33 | 0.83 | 2.17 | 0.00 | 1.60 | 0.20 | 1.17 | 0.00 | 0.00 | 45.67 | 28.58 |
| SD | | 1.03 | 0.75 | 0.82 | 0.52 | 0.75 | 0.75 | 0.00 | 0.89 | 0.45 | 0.75 | 0.00 | 0.00 | 18.02 | 7.85 |

| Group | | TNF-a | | | | IL-17 IgM | | | | IL-10 | | | | IL-1b | | | |
|---|---|---|---|---|---|---|---|---|---|---|---|---|---|---|---|---|---|
| Joint | | Left | | | | | | | | | | | | | | | |
| Tissue | Sheep | intima | Left tissue | Right intima | Right tissue | Left intima | Left tissue | Right intima | Right tissue | Left intima | Left tissue | Right intima | Right tissue | Left intima | Left tissue | Right intima | Right tissue |
| F (Saline) IA | Y28 | no intima | 0 | 1 | 0 | no intima | 3 | 1 | 0 | no intima | 0 | 0 | 0 | no intima | 1 | 1 | 0 |
| | Y31 | 2 | 2 | 0 | 0 | 3 | 4 | 2 | 2 | 0 | 0 | 0 | 0 | 1 | 1 | 0 | 0 |
| | Y30 | 1 | 1 | 1 | 1 | 2 | 2 | 2 | 1 | 0 | 0 | 0 | 0 | 1 | 0 | 0 | 0 |
| | Y34 | no intima | 1 | no intima | 0 | 2 | 3 | no intima | 1 | no intima | 0 | no intima | 0 | no intima | 2 | no intima | 0 |
| | Y37 | 0 | 0 | 0 | 0 | 3 | 3 | 1 | 1 | 0 | 0 | 0 | 0 | 1 | 0 | 0 | 0 |
| | Y39 | 1 | 1 | 1 | 0 | 2 | 3 | 1 | 1 | 0 | 0 | 0 | 0 | 0 | 0 | 0 | 0 |
| mean | | 1.00 | 0.83 | 0.60 | 0.17 | 2.40 | 3.00 | 1.40 | 1.00 | 0.00 | 0.00 | 0.00 | 0.00 | 0.75 | 0.67 | 0.20 | 0.00 |
| SD | | 0.82 | 0.75 | 0.55 | 0.41 | 0.55 | 0.63 | 055 | 0.63 | 0.00 | 0.00 | 0.00 | 0.00 | 0.50 | 0.82 | 0.45 | 0.00 |
| E(MPC) IA | Y26 | 0 | 0 | 0 | 0 | 1 | 1 | 0 | 1 | 0 | 0 | no intima | 0 | 0 | 0 | no intima | 0 |
| | Y27 | 0 | 0 | 0 | 0 | 1 | 2 | 2 | 0 | 0 | 0 | 0 | 0 | 0 | 0 | 1 | 0 |
| | Y29 | 1 | 1 | 0 | 0 | 2 | 3 | 1 | 1 | 1 | 0 | 0 | 0 | 1 | 0 | 0 | 0 |
| | Y32 | 0 | 1 | 0 | 0 | 1 | 2 | 1 | 1 | 0 | 0 | 0 | 0 | 0 | 0 | 0 | 0 |
| | Y38 | 1 | 0 | 0 | 0 | 2 | 3 | 2 | 3 | 0 | 0 | 0 | 0 | 0 | 0 | 0 | 0 |
| | Y40 | 1 | 0 | | | 3 | 3 | 2 | 2 | 0 | 0 | 0 | 0 | 1 | 0 | 0 | 0 |
| mean | | 0.50 | 0.33 | 0.00 | 0.00 | 1.67 | 2.33 | 1.33 | 1.33 | 0.17 | 0.00 | 0.00 | 0.00 | 0.17 | 0.17 | 0.20 | 0.00 |
| SD | | 0.55 | 0.52 | 0.00 | 0.00 | 0.82 | 0.82 | 0.82 | 1.03 | 0.41 | 0.00 | 0.00 | 0.00 | 0.41 | 0.41 | 0.45 | 0.00 |

General Discussion

As disclosed herein, immunization of adult sheep by the SC injection of bovine type II collagen in Freund's complete and incomplete adjuvant, followed by intra-articular (IA) injection of the same protein alone into their hock joints, resulted in the induction of an arthropathy that displayed many of the classical pathological hallmarks of human RA.

This ovine model of RA was therefore considered to be suitable for the evaluation of the therapeutic effects of IV administered MPC at the doses of $0.3 \times 10^6$ cells/kg, $1.0 \times 10^6$ cells/kg and $2.0 \times 10^6$ cells/kg relative to the effects of an equivalent volume of IV saline. For comparative purposes an IA group that received a single injection of $25 \times 10^6$ MPC or saline into the left hock joints was also included in the study. MPCs or saline were administered 14 days following the intra-articular injection of bovine type II collagen (day 28) and sacrificed 30 days later. (day 72).

The outcomes from the analysis of the histopathological and immunohistochemical analysis of synovial tissues were positive. Moreover, of the three IV MPC doses administered, the highest dose of 2 million MPC/kg consistently generated statistical improvements relative to the saline control group. While the low dose MPC group also showed positive effects in some of the parameters studied, the mid dose MPC treated exhibited a mixed response. The reason for the absence of a clear dose response relationship in the present study is not entirely clear but may be related to the small number of animals used in each group and the heterogeneity in the intensity of disease expression within the group as exemplified by the high standard deviations observed for many of the control group parameters. Nevertheless, the statistically significant reduction of histopathological scores observed for the synovial membranes of the left hock joints from the high dose MPC groups relative to saline controls (FIG. 8C) were supported by the reduced immunohistochemical scores for synoviocyte (intima) staining for IL-6, TNF-alpha (FIG. 4D) and interstitial tissue staining for CD14 cells (FIG. 10E) and IL-17 (FIG. 10F).

The results of the present studies using an ovine model of chronic RA have confirmed that a single IV injection of between 0.3-2.0 million MPC/kg was effective in reducing the key histopathological indices of arthritis, namely, synovial hyperplasia, stromal tissue activation and inflammatory cell infiltration. Moreover the demonstration, using immunohistochemical staining of frozen sections, that the levels of IL-6, TNF-alpha, IL-17 and CD14+ cells were significantly reduced in the high MPC dosed animals, relative to the saline control's was supportive of our working hypothesis. IL-17 has been shown (Shahrara et al. (2009) *Journal of Immunology* 182: 3884-3891) to induce monocyte migration in vivo leading to suggest that this cytokine was responsible for the recruitment of monocytes into the joints of patients with RA. This view was consistent with our hypothesis that by reducing the levels of IL-17 in the synovial interstitium, the injected MPC indirectly diminished the numbers of monocytes migrating from the bone marrow to the inflamed joint thereby limiting the levels of pro-inflammatory cytokines, such as IL-6 and TNF-alpha produced by the synoviocytes of the proliferating intima.

Moreover, "conventional" inflammatory cytokines expressed in cartilage and synovium have been suggested to play a role in osteoarthritis, including and interleukin-1β (IL-1 β), tumor necrosis factor alpha (TNFα), IL-6, IL-8, IL-17 and soluble CD14 (Liu-Bryan and Terkeltaub *Arthritis and Rheumatism,* 64: 2055-2058, 2012). Thus, the data presented herein support a role for the administration of MPCs (e.g., intravenously) to treat osteoarthritis.

The invention claimed is:

1. A method for treating a rheumatic disease in a subject, the method comprising systemically administering to the subject an effective amount of a population of cells enriched for STRO-1+ cells, thereby reducing the level of any one or more of IL-6, TNF-α, IL-17 and/or CD14+ cells in a joint of the subject, wherein the STRO-1+ cells are STRO-1+ multipotential cells.

2. The method of claim 1, wherein the rheumatic disease is selected from the group consisting of rheumatoid arthritis, Still's disease, ankylosing spondylitis, Reiter's disease, psoriatric arthritis, enteric arthritis, sacroiliitis, spondylitis and osteoarthritis.

3. The method of claim 1, wherein the rheumatic disease is rheumatoid arthritis.

4. The method of claim 1, wherein the subject is receiving treatment with methotrexate prior to administration of the population of cells enriched for STRO-1+ cells.

5. The method of claim 1 comprising administering a population of cells enriched for STRO-1$^{bright}$ cells.

6. The method of claim 1, comprising:
(i) administering between $0.1 \times 10^6$ to $5 \times 10^6$ STRO-1+ cells per kilogram;
(ii) administering between $0.3 \times 10^6$ cells/kg to $2 \times 10^6$ cells/kg, wherein the cells are STRO-1+ cells
(iii) administering a low dose of STRO-1+ cells.

7. The method of claim 6, wherein the low dose of STRO-1+ cells comprises between $0.1 \times 10^5$ and $0.5 \times 10^6$ STRO-1+ cells per kilogram or comprises about $0.3 \times 10^6$ STRO-1+ cells per kilogram.

8. The method of claim 1 comprising administering a high dose of STRO-1+ cells, comprising between about $1.5 \times 10^5$ to about $2 \times 10^6$ STRO-1+ cells per kilogram.

9. The method of claim 1, wherein the dose of STRO-1+ cells comprises a dose of between about 100 million cells to about 300 million cells.

10. The method of claim 1, wherein the population enriched for STRO-1+ cells are administered once weekly or less often.

11. The method of claim 1, wherein the population enriched for STRO-1$^{30}$ cells are administered once every four weeks or less often.

12. The method of claim 1, wherein the population enriched for STRO-1$^+$ cells are administered intra-arterially, into an aorta, into an atrium or ventricle of the heart or intravenously.

13. The method of claim 1, wherein the population enriched for STRO-1$^+$ cells are autogeneic or allogeneic.

14. The method of claim 1, wherein the population enriched for STRO-1$^+$ cells have been culture expanded prior to administration.

15. The method of claim 1, wherein the population enriched for STRO-1$^+$ cells are STRO-1$^{bri}$, and/or express tissue non-specific alkaline phosphatase (TNAP).

16. The method according to claim 1, wherein the STRO-1$^+$ cells are administered in the form of a composition comprising said STRO-1$^+$ cells and a carrier and/or excipient.

\* \* \* \* \*

SEQUENCE LISTING

<160> NUMBER OF SEQ ID NOS: 36

<210> SEQ ID NO 1
<211> LENGTH: 20
<212> TYPE: DNA
<213> ORGANISM: artificial
<220> FEATURE:
<223> OTHER INFORMATION: oligonucleotide for amplifying GAPDH

<400> SEQUENCE: 1
cactgacacg ttggcagtgg                                              20

<210> SEQ ID NO 2
<211> LENGTH: 20
<212> TYPE: DNA
<213> ORGANISM: artificial
<220> FEATURE:
<223> OTHER INFORMATION: oligonucleotide for amplifying GAPDH

<400> SEQUENCE: 2
catggagaag gctggggctc                                              20

<210> SEQ ID NO 3
<211> LENGTH: 20
<212> TYPE: DNA
<213> ORGANISM: artificial
<220> FEATURE:
<223> OTHER INFORMATION: oligonucleotide for amplifying SDF-1

<400> SEQUENCE: 3
gagacccgcg ctcgtccgcc                                              20

<210> SEQ ID NO 4
<211> LENGTH: 21
<212> TYPE: DNA
<213> ORGANISM: artificial
<220> FEATURE:
<223> OTHER INFORMATION: oligonucleotide for amplifying SDF-1

<400> SEQUENCE: 4
gctggactcc tactgtaagg g                                            21

<210> SEQ ID NO 5
<211> LENGTH: 22
<212> TYPE: DNA
<213> ORGANISM: artificial
<220> FEATURE:
<223> OTHER INFORMATION: oligonucleotide for amplifying IL-1beta

<400> SEQUENCE: 5
aggaagatgc tggttccctc tc                                           22

```
<210> SEQ ID NO 6
<211> LENGTH: 23
<212> TYPE: DNA
<213> ORGANISM: artificial
<220> FEATURE:
<223> OTHER INFORMATION: oligonucleotide for amplifying IL-1beta

<400> SEQUENCE: 6
cagttcagtg atcgtacagg tgc                                          23

<210> SEQ ID NO 7
<211> LENGTH: 29
<212> TYPE: DNA
<213> ORGANISM: artificial
<220> FEATURE:
<223> OTHER INFORMATION: oligonucleotide for amplifying FLT-1

<400> SEQUENCE: 7
tcactatgga agatctgatt tcttacagt                                    29

<210> SEQ ID NO 8
<211> LENGTH: 25
<212> TYPE: DNA
<213> ORGANISM: artificial
<220> FEATURE:
<223> OTHER INFORMATION: oligonucleotide for amplifying FLT-1

<400> SEQUENCE: 8
ggtataaata cacatgtgct tctag                                        25

<210> SEQ ID NO 9
<211> LENGTH: 20
<212> TYPE: DNA
<213> ORGANISM: artificial
<220> FEATURE:
<223> OTHER INFORMATION: oligonucleotide for amplifying TNFalpha

<400> SEQUENCE: 9
tcagatcatc ttctcgaacc                                              20

<210> SEQ ID NO 10
<211> LENGTH: 20
<212> TYPE: DNA
<213> ORGANISM: artificial
<220> FEATURE:
<223> OTHER INFORMATION: oligonucleotide for amplifying TNFalpha

<400> SEQUENCE: 10
cagatagatg ggctcatacc                                              20

<210> SEQ ID NO 11
<211> LENGTH: 20
<212> TYPE: DNA
<213> ORGANISM: artificial
<220> FEATURE:
<223> OTHER INFORMATION: oligonucleotide for amplifying KDR

<400> SEQUENCE: 11
tatagatggt gtaacccgga                                              20

<210> SEQ ID NO 12
<211> LENGTH: 21
<212> TYPE: DNA
<213> ORGANISM: artificial
<220> FEATURE:
<223> OTHER INFORMATION: oligonucleotide for amplifying KDR
```

```
<400> SEQUENCE: 12
tttgtcactg agacagcttg g                                          21

<210> SEQ ID NO 13
<211> LENGTH: 21
<212> TYPE: DNA
<213> ORGANISM: artificial
<220> FEATURE:
<223> OTHER INFORMATION: oligonucleotide for amplifying RANK-ligand

<400> SEQUENCE: 13
aacaggcctt tcaaggagct g                                          21

<210> SEQ ID NO 14
<211> LENGTH: 22
<212> TYPE: DNA
<213> ORGANISM: artificial
<220> FEATURE:
<223> OTHER INFORMATION: oligonucleotide for amplifying RANK-ligand

<400> SEQUENCE: 14
taaggagggg ttggagacct cg                                         22

<210> SEQ ID NO 15
<211> LENGTH: 20
<212> TYPE: DNA
<213> ORGANISM: artificial
<220> FEATURE:
<223> OTHER INFORMATION: oligonucleotide for amplifying Leptin

<400> SEQUENCE: 15
atgcattggg aaccctgtgc                                            20

<210> SEQ ID NO 16
<211> LENGTH: 20
<212> TYPE: DNA
<213> ORGANISM: artificial
<220> FEATURE:
<223> OTHER INFORMATION: oligonucleotide for amplifying Leptin

<400> SEQUENCE: 16
gcacccaggg ctgaggtcca                                            20

<210> SEQ ID NO 17
<211> LENGTH: 21
<212> TYPE: DNA
<213> ORGANISM: artificial
<220> FEATURE:
<223> OTHER INFORMATION: oligonucleotide for amplifying CBFA-1

<400> SEQUENCE: 17
gtggacgagg caagagtttc a                                          21

<210> SEQ ID NO 18
<211> LENGTH: 21
<212> TYPE: DNA
<213> ORGANISM: artificial
<220> FEATURE:
<223> OTHER INFORMATION: oligonucleotide for amplifying CBFA-1

<400> SEQUENCE: 18
tggcaggtag gtgtggtagt g                                          21

<210> SEQ ID NO 19
```

```
<211> LENGTH: 28
<212> TYPE: DNA
<213> ORGANISM: artificial
<220> FEATURE:
<223> OTHER INFORMATION: oligonucleotide for amplifying PPARgamma2

<400> SEQUENCE: 19
aactgcgggg aaacttggga gattctcc                                            28

<210> SEQ ID NO 20
<211> LENGTH: 26
<212> TYPE: DNA
<213> ORGANISM: artificial
<220> FEATURE:
<223> OTHER INFORMATION: oligonucleotide for amplifying PPARgamma2

<400> SEQUENCE: 20
aataataagg tggagatgca ggctcc                                              26

<210> SEQ ID NO 21
<211> LENGTH: 21
<212> TYPE: DNA
<213> ORGANISM: artificial
<220> FEATURE:
<223> OTHER INFORMATION: oligonucleotide for amplifying OCN

<400> SEQUENCE: 21
atgagagccc tcacactcct c                                                   21

<210> SEQ ID NO 22
<211> LENGTH: 19
<212> TYPE: DNA
<213> ORGANISM: artificial
<220> FEATURE:
<223> OTHER INFORMATION: oligonucleotide for amplifying OCN

<400> SEQUENCE: 22
cgtagaagcg ccgataggc                                                      19

<210> SEQ ID NO 23
<211> LENGTH: 20
<212> TYPE: DNA
<213> ORGANISM: artificial
<220> FEATURE:
<223> OTHER INFORMATION: oligonucleotide for amplifying MyoD

<400> SEQUENCE: 23
aagcgccatc tcttgaggta                                                     20

<210> SEQ ID NO 24
<211> LENGTH: 20
<212> TYPE: DNA
<213> ORGANISM: artificial
<220> FEATURE:
<223> OTHER INFORMATION: oligonucleotide for amplifying MyoD

<400> SEQUENCE: 24
gcgagaaacg tgaacctagc                                                     20

<210> SEQ ID NO 25
<211> LENGTH: 20
<212> TYPE: DNA
<213> ORGANISM: artificial
<220> FEATURE:
<223> OTHER INFORMATION: oligonucleotide for amplifying SMMHC

<400> SEQUENCE: 25
```

-continued

```
ctgggcaacg tagtaaaacc                                          20

<210> SEQ ID NO 26
<211> LENGTH: 20
<212> TYPE: DNA
<213> ORGANISM: artificial
<220> FEATURE:
<223> OTHER INFORMATION: oligonucleotide for amplifying SMMHC

<400> SEQUENCE: 26
tatagctcat tgcagcctcg                                          20

<210> SEQ ID NO 27
<211> LENGTH: 21
<212> TYPE: DNA
<213> ORGANISM: artificial
<220> FEATURE:
<223> OTHER INFORMATION: oligonucleotide for amplifying GFAP

<400> SEQUENCE: 27
ctgttgccag agatggaggt t                                        21

<210> SEQ ID NO 28
<211> LENGTH: 20
<212> TYPE: DNA
<213> ORGANISM: artificial
<220> FEATURE:
<223> OTHER INFORMATION: oligonucleotide for amplifying GFAP

<400> SEQUENCE: 28
tcatcgctca ggaggtcctt                                          20

<210> SEQ ID NO 29
<211> LENGTH: 24
<212> TYPE: DNA
<213> ORGANISM: artificial
<220> FEATURE:
<223> OTHER INFORMATION: oligonucleotide for amplifying nestin

<400> SEQUENCE: 29
ggcagcgttg gaacagaggt tgga                                     24

<210> SEQ ID NO 30
<211> LENGTH: 24
<212> TYPE: DNA
<213> ORGANISM: artificial
<220> FEATURE:
<223> OTHER INFORMATION: oligonucleotide for amplifying nestin

<400> SEQUENCE: 30
ctctaaactg gagtggtcag ggct                                     24

<210> SEQ ID NO 31
<211> LENGTH: 21
<212> TYPE: DNA
<213> ORGANISM: artificial
<220> FEATURE:
<223> OTHER INFORMATION: oligonucleotide for amplifying SOX9

<400> SEQUENCE: 31
ctctgcctgt ttggactttg t                                        21

<210> SEQ ID NO 32
<211> LENGTH: 21
<212> TYPE: DNA
```

```
<213> ORGANISM: artificial
<220> FEATURE:
<223> OTHER INFORMATION: oligonucleotide for amplifying SOX9

<400> SEQUENCE: 32
cctttgcttg cctttttacct c                                              21

<210> SEQ ID NO 33
<211> LENGTH: 20
<212> TYPE: DNA
<213> ORGANISM: artificial
<220> FEATURE:
<223> OTHER INFORMATION: oligonucleotide for amplifying collagen type X

<400> SEQUENCE: 33
agccagggtt gccaggacca                                                 20

<210> SEQ ID NO 34
<211> LENGTH: 20
<212> TYPE: DNA
<213> ORGANISM: artificial
<220> FEATURE:
<223> OTHER INFORMATION: oligonucleotide for amplifying collagen type X

<400> SEQUENCE: 34
ttttcccact ccaggagggc                                                 20

<210> SEQ ID NO 35
<211> LENGTH: 20
<212> TYPE: DNA
<213> ORGANISM: artificial
<220> FEATURE:
<223> OTHER INFORMATION: oligonucleotide for amplifying aggrecan

<400> SEQUENCE: 35
cactgttacc gccacttccc                                                 20

<210> SEQ ID NO 36
<211> LENGTH: 20
<212> TYPE: DNA
<213> ORGANISM: artificial
<220> FEATURE:
<223> OTHER INFORMATION: oligonucleotide for amplifying aggrecan

<400> SEQUENCE: 36
accagcggaa gtccccttcg                                                 20
```